United States Patent [19]

Soares et al.

[11] Patent Number: 5,846,721
[45] Date of Patent: Dec. 8, 1998

[54] EFFICIENT AND SIMPLER METHOD TO CONSTRUCT NORMALIZED CDNA LIBRARIES WITH IMPROVED REPRESENTATIONS OF FULL-LENGTH CDNAS

[75] Inventors: Marcelo Bento Soares; Maria de Fatima Bonaldo, both of New York, N.Y.

[73] Assignee: The Trustees of Columbia University in the City of New York, New York, N.Y.

[21] Appl. No.: 715,941

[22] Filed: Sep. 19, 1996

[51] Int. Cl.[6] .............................. C12Q 1/68; C12P 19/34
[52] U.S. Cl. .......................... 435/6; 435/91.1; 435/91.2; 536/25.4
[58] Field of Search ............................ 435/6, 91.1, 91.2; 536/25.4

[56] References Cited

U.S. PATENT DOCUMENTS

| 5,482,845 | 1/1996 | Soares et al. | 435/91.1 |
| 5,565,340 | 10/1996 | Chenchik et al. | 435/91.2 |
| 5,637,685 | 6/1997 | Soares et al. | 536/23.1 |
| 5,702,898 | 12/1997 | Bonaldo et al. | 435/6 |

OTHER PUBLICATIONS

Sasaki et al., Nucleic Acids Res. 22(6), 987–992 (1994).
Bonaldo et al., Genome Res. 6(9), 791–806 (Sep. 1996).
Soares et al., Proc. Natl. Acad. Sci. USA 91, 9228–9232 (1994).
Patanjali et al., Proc. Natl. Acad. Sci. USA 88, 1943–1947 (1991).
Ko, Nucleic Acids Res. 18(19), 5705–5711 (1990).
Adams, M.D. et al. (1991) *Science* 252:1651–1656 (Exhibit C).
Adams, M.D. et al. (1992) *Nature* 355:632–634 (Exhibit D).
Adams, M.D. et al. (1993) *Nature Genetics* 4:256–267 (Exhibit E).

(List continued on next page.)

*Primary Examiner*—Kenneth R. Horlick
*Attorney, Agent, or Firm*—John P. White; Cooper & Dunham LLP

[57] ABSTRACT

This invention provides a method to normalize a cDNA library comprising: (a) constructing a directionally cloned library containing cDNA inserts wherein the insert is capable of being amplified by polymerase chain reaction; (b) converting a double-stranded cDNA library into single-stranded DNA circles; (c) generating single-stranded nucleic acid molecules complementary to the single-stranded DNA circles converted in step (b) by polymerase chain reaction with appropriate primers; (d) hybridizing the single-stranded DNA circles converted in step (b) with the complementary single-stranded nucleic acid molecules generated in step (c) to produce partial duplexes to an appropriate Cot; and (e) separating the unhybridized single-stranded DNA circles from the hybridized DNA circles, thereby generating a normalized cDNA library. This invention also provides a method to normalize a cDNA library wherein the generating of single-stranded nucleic acid molecules complementary to the single-stranded DNA circles converted in step (b) is by excising cDNA inserts from the double-stranded cDNA library; purifying the cDNA inserts from cloning vectors; and digesting the cDNA inserts with an exonuclease. This invention further provides a method to construct a subtractive cDNA library following the steps described above. This invention further provides normalized and/or subtractive cDNA libraries generated by the above methods.

30 Claims, 7 Drawing Sheets

OTHER PUBLICATIONS

Adams et al. (1993) *Nature Genetics* 4:373–380 (Exhibit F).
Altschul, S.F. et al. (1990) *J. Mol. Biol.* 215:403–410 (Exhibit G).
Barnes, W.M. (1994) *Proc. Natl. Acad. Sci. USA* 91:2216–2220 (Exhibit H).
Berry, R. et al. (1995) *Nature Genetics* 10:415–423 (Exhibit I).
Bishop, J.O. et al. (1974) *Science* 250:199–204 (Exhibit J).
Davidson, E.H. and Britten, R.J. (1979) *Science* 204:1052–1059 (Exhibit K).
Haraguchi, Y. et al. (1987) *Proc. Natl. Acad. Sci. USA* 84:412–415 (Exhibit L).
Hoheisel, J.D. (1993) *Anal. Biochem.* 209:238–246 (Exhibit M).
Ko, M.S.H. (1990) *Nucl. Acids Res.* 18(19):5705–5711 (Exhibit N).
Patanjali, S.R. et al. (1991) *Proc. Natl. Acad. Sci. USA* 88:1943–1947 (Exhibit O).
Sasaki, Y.F. (1994) *Nucl. Acids Res.* 22(6):987–992 (Exhibit P).
Soares, M.B. et al. (1992) *NTIS* (Exhibit Q).

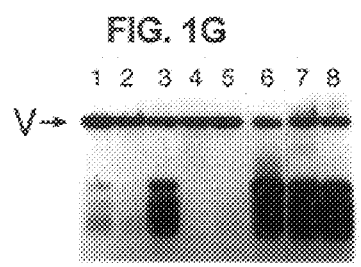
FIG. 1G
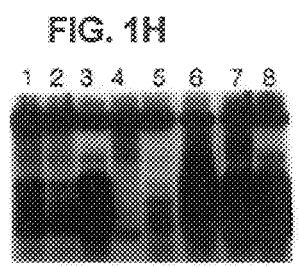
FIG. 1H
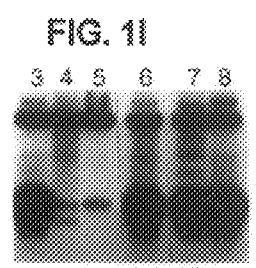
FIG. 1I
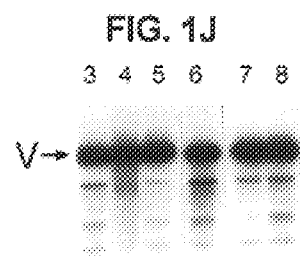
FIG. 1J
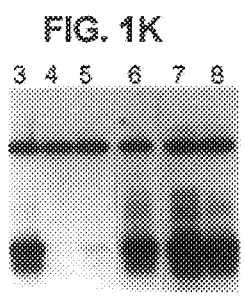
FIG. 1K
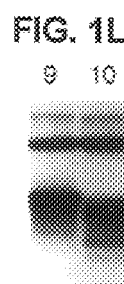
FIG. 1L
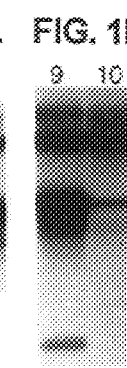
FIG. 1M
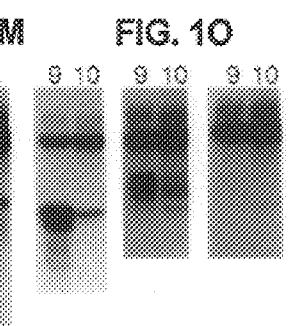
FIG. 1O
FIG. 1N  FIG. 1P

EFFICIENT AND SIMPLER METHOD TO CONSTRUCT NORMALIZED CDNA LIBRARIES WITH IMPROVED REPRESENTATIONS OF FULL-LENGTH CDNAS

This invention was made with support under Grant Number DE-FG02-91ER61233 from the U.S. Department of Energy, and Grant Number 1RO1HG00980 from the National Center for Human Genome Research. Accordingly, the U.S. Government has certain rights in the invention.

Throughout this application, various references are referred to by last names of the first authors within parenthesis. Disclosures of these publications in their entireties are hereby incorporated by reference into this application to more fully describe the state of the art to which this invention pertains. Full bibliographic citation for these references may be found immediately preceding the claims.

BACKGROUND OF THE INVENTION

Large scale single-pass sequencing of cDNA clones randomly picked from libraries has proven to be a powerful approach to discover genes (Adams et al. 1992; Adams et al. 1991; Adams et al. 1993a; Adams et al. 1995; Adams et al. 1993b; Khan et al. 1992; Matsubara and Okubo 1993; McCombie et al. 1992; Okubo et al. 1992; Hillier et al. 1996 (in press). However, the significance of using cDNA libraries that are well suited for this purpose should not be underestimated (Adams et al. 1993b).

Ordinary cDNA libraries may contain a high frequency of undesirable ("junky") clones (Adams et al. 1992; Adams et al. 1991) which may not only drastically impair the overall efficiency of the approach, but also seriously compromise the integrity of the data that are generated. Among such "junky" clones are those that (i) consist exclusively of poly(A) tails of mRNAs, (ii) contain very short cDNA inserts, (iii) contain nothing but the 3' half of the Not I-oligo $[dT]_{18}$ primer used for synthesis of first-strand cDNA ligated to an adaptor, as well as (iv) chimeric clones, i.e. cDNAs derived from different mRNAs artifactually joined during ligation (Soares 1994). Furthermore, given that, as a general rule, the frequency of occurrence of a cDNA clone in a library is equivalent to that of its corresponding mRNA in the cell, even high quality cDNA libraries may not be ideal for large scale sequencing.

Reassociation-kinetics analysis indicates that the mRNAs of a typical somatic cell are distributed in three frequency classes: (I) superprevalent [consisting of about 10–15 mRNAs which altogether represent 10–20% of the total mRNA mass], (II) intermediate [1–2,000 mRNAs; 40–45%] and (III) complex [15–20,000 mRNAs; 40–45%] (Bishop et al. 1974; Davidson and Britten 1979). Accordingly, once most mRNAs of the prevalent and intermediate frequency classes are identified, redundancy levels are expected to become greater than 60%. For this reason the use of normalized libraries, in which the frequency of all clones is within a narrow range (Soares et al. 1994), has been shown to be advantageous for large scale sequencing (Berry et al. 1995; Houlgatte et al. 1995). Calculations show that at $C_0t$ 5.5, of the three kinetic classes of mRNAs, the most abundant species are drastically diminished, while all frequencies are brought within the range of one order of magnitude (Soares et al., 1994). However, since a large fraction of all human genes has been identified already, redundant identification of genes that are expressed in multiple tissues cannot be avoided simply by the use of normalized libraries.

Hence, the use of subtractive cDNA libraries enriched for genes expressed at low levels and that have not yet been identified should become increasingly more advantageous for large scale sequencing programs.

While attempting to improve the representation of full-length transcripts in cDNA libraries three methods were developed for construction of normalized libraries, in addition to the procedure that was described previously (Soares et al. 1994), and was successfully used to generate normalized cDNA libraries from human (15), mouse (3), rat (2), and Schistosoma mansoni (1) tissues. All human and mouse cDNA libraries have been contributed to the I.M.A.G.E. Consortium (Lennon et al. 1996), and up to date a total of 315,408 ESTs have been derived from these libraries (dbEST release 052396; http://www.ncbi.nlm.nih.gov).

Here a detailed description and a comparative analysis of the four methods that have been developed to normalize cDNA libraries is presented, a simple procedure for the construction of subtractive cDNA libraries is described, and strategies that take advantage of subtractive hybridization to expedite the ongoing I.M.A.G.E./Washington University/ Merck gene discovery program is discussed.

SUMMARY OF THE INVENTION

This invention provides a method to normalize a cDNA library comprising: (a) constructing a directionally cloned library containing cDNA inserts wherein the insert is capable of being amplified by polymerase chain reaction; (b) converting a double-stranded cDNA library into single-stranded DNA circles; (c) generating single-stranded nucleic acid molecules complementary to the single-stranded DNA circles converted in step (b) by polymerase chain reaction with appropriate primers; (d) hybridizing the single-stranded DNA circles converted in step (b) with the complementary single-stranded nucleic acid molecules generated in step (c) to produce partial duplexes to an appropriate Cot; and (e) separating the unhybridized single-stranded DNA circles from the hybridized DNA circles, thereby generating a normalized cDNA library.

This invention also provides a method to normalize a cDNA library comprising: (a) constructing a directionally cloned library containing cDNA inserts; (b) converting a double-stranded cDNA library into single-stranded DNA circles; (c) generating single-stranded nucleic acid molecules complementary to the single-stranded DNA circles converted in step (b) by excising cDNA inserts from the double-stranded cDNA library; purifying the cDNA inserts from cloning vectors; and digesting the cDNA inserts with an exonuclease; (d) hybridizing the single-stranded DNA circles converted in step (b) with the complementary single-stranded nucleic acid molecules generated in step (c) to produce partial duplexes to an appropriate Cot; and (e) separating the unhybridized single-stranded DNA circles from the hybridized DNA circles, thereby generating a normalized cDNA library.

This invention further provides a method to construct a subtractive cDNA library comprising: (a) converting of a double-stranded cDNA library into single-stranded DNA circles; (b) treating a pool of double-stranded DNAs which are to be eliminated from the subtractive cDNA library with a site-specific endonuclease and an exonuclease to generate single-stranded DNA molecules; (c) separating the single-stranded DNA molecules from the double-stranded DNAs; (d) amplifying the separated single-stranded DNA molecules by PCR; (e) hybridizing the single-stranded DNA circles converted in step (a) with single-stranded DNA molecules generated in step (b) to produce partial duplexes to an appropriate Cot; and (f) separating the unhybridized single-stranded DNA circles from the hybridized DNA circles, thereby generating a subtractive cDNA library.

This invention further provides normalized and/or subtractive cDNA libraries generated by the above methods.

Double-stranded plasmid DNA representing an entire starting library is (I) linearized with either Sfi I, Not I, or Pac I and used as template for synthesis of RNA in vitro using T3 or T7 RNA Polymerases, and (ii) converted to single-stranded circles either in vivo, upon electroporation into DH5αF' and superinfection with M13KO7, or in vitro by the combined action of Gene II and Exonuclease III (Life Technologies). Single-stranded plasmid DNA is HAP purified and hybridized ($C_0t$~5) with excess RNA (pre-treated with RNAse free DNAse I; Promega), blocked with appropriate oligonucleotides to prevent hybridization through common vector sequences (see Methods section). Both the fraction that remains single-stranded (flow-through) as well as the resulting hybrids (bound) are purified by HAP chromatography. The HAP-flow-through fraction is converted to double-stranded plasmids, electroporated into DH10B bacteria (Life Technologies) and propagated under ampicillin selection to generate an amplified normalized library (methods 2-1 and 2-2, depending on the conditions used for hybridization; see Methods section). The HAP-bound fraction is also similarly converted to double-stranded plasmids, electroporated into bacteria and propagated under ampicillin selection to generate a mini-library enriched for abundant cDNAs (see Table 3). Double-stranded plasmid DNA from this mini-library is linearized and used as template for synthesis of RNA in vitro. After digestion of the plasmid DNA template with RNAse free DNAse I (Promega), the RNA (driver) is blocked with appropriate oligonucleotides and hybridized to an appropriate $C_0t$ ($C_0t$~100–200) with HAP-purified single-stranded plasmids derived from the starting library (see above). The remaining single-stranded circles are purified by HAP chromatography, converted to double-stranded circles, electroporated into DH10B (Life Technologies) and propagated under ampicillin selection to generate an amplified normalized library (method 2-3).

Figure 3A:
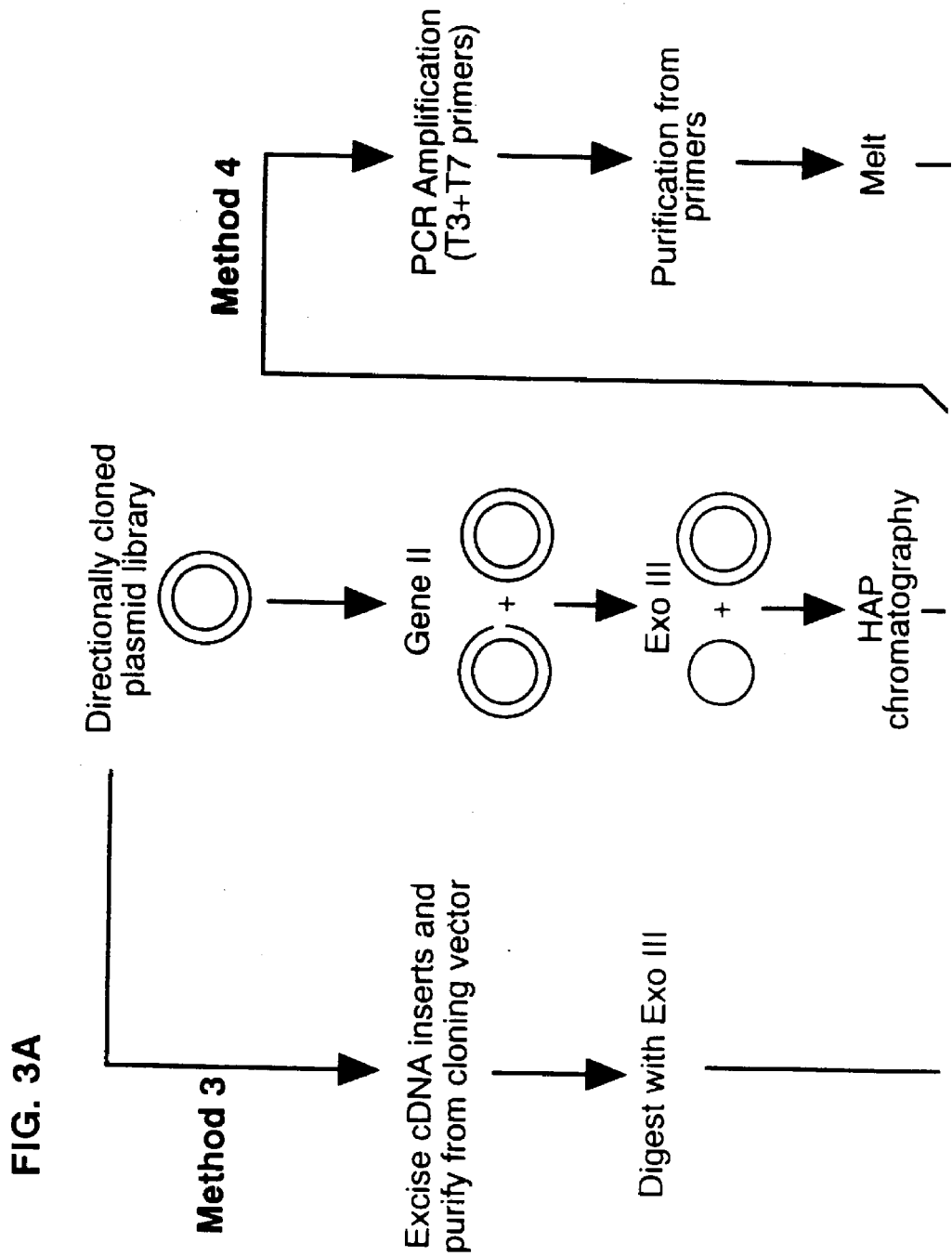
Figure 3B:
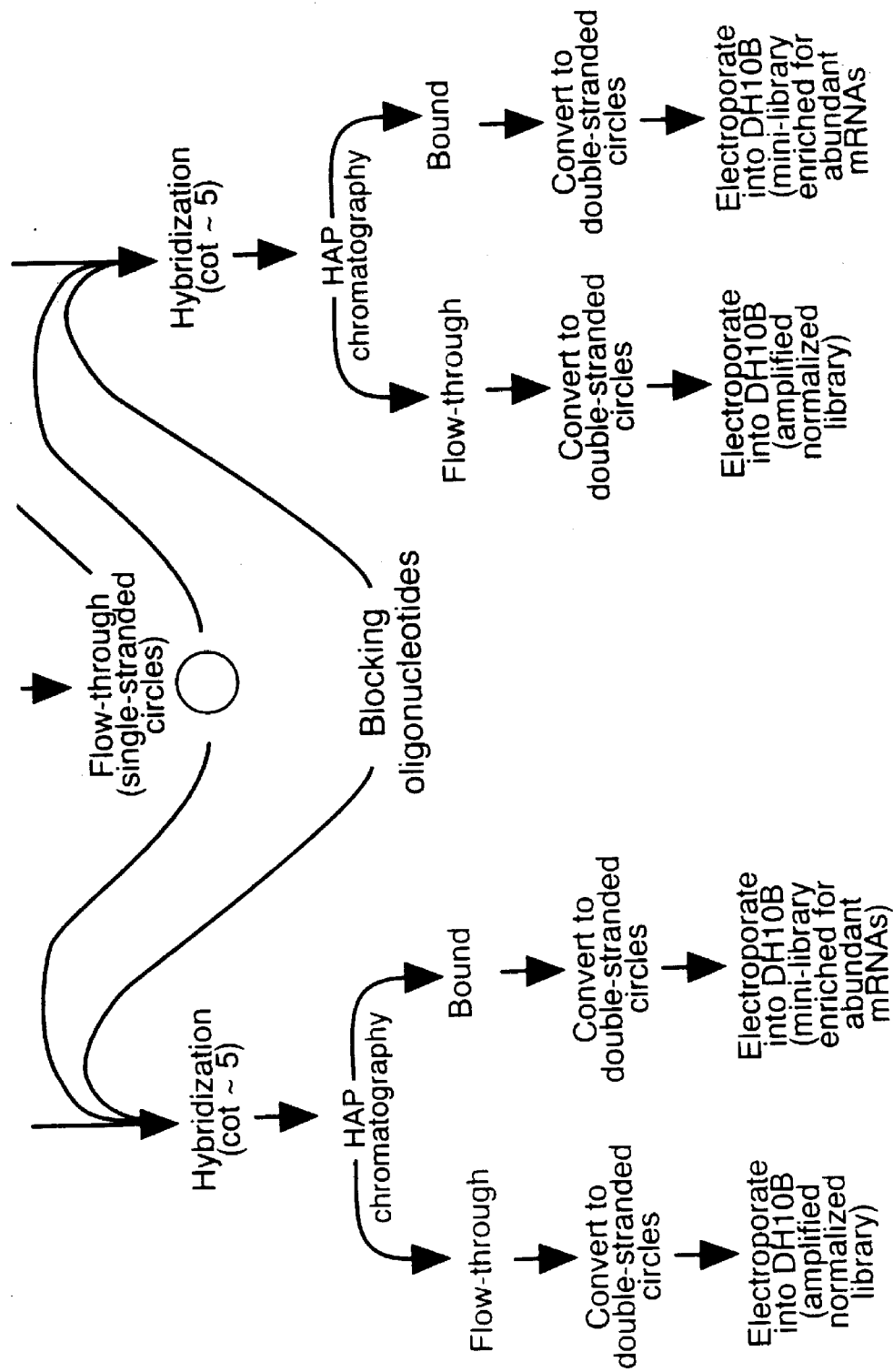

FIGS. 3A–3B Diagram of the normalization methods 3 and 4

In Method 3 (left column) double-stranded plasmid DNA from a starting library is digested with restriction enzymes that generate 5' protruding ends, the excised cDNA inserts are gel purified from the cloning vector, and digested with Exonuclease III to yield non complementary single-stranded fragments each representing a half of a cDNA insert. Note that the single-stranded fragments that span the 5' half (but not the 3' half) of the cDNA inserts are complementary to single-stranded plasmids prepared in vitro. These single-stranded DNA fragments are blocked with appropriate oligonucleotides (see Methods) and hybridized with single-stranded library DNA prepared in vitro (middle column). The remaining single-stranded circles are HAP-purified, converted to double-stranded plasmids, electroporated into DH10B bacteria (Life Technologies) and propagated under ampicillin selection to generate a normalized library. In Method 4 (right column), single-stranded library DNA is used as template for PCR amplification with T3 and T7 primers. PCR-amplified cDNAs are purified from excess primers, melted and hybridized with single-stranded library DNA in the presence of blocking oligonucleotides. The remaining single-stranded circles are purified by HAP chromatography, converted to double-stranded plasmids, electroporated into bacteria and propagated under ampicillin selection to generate a normalized library.

Figure 4:
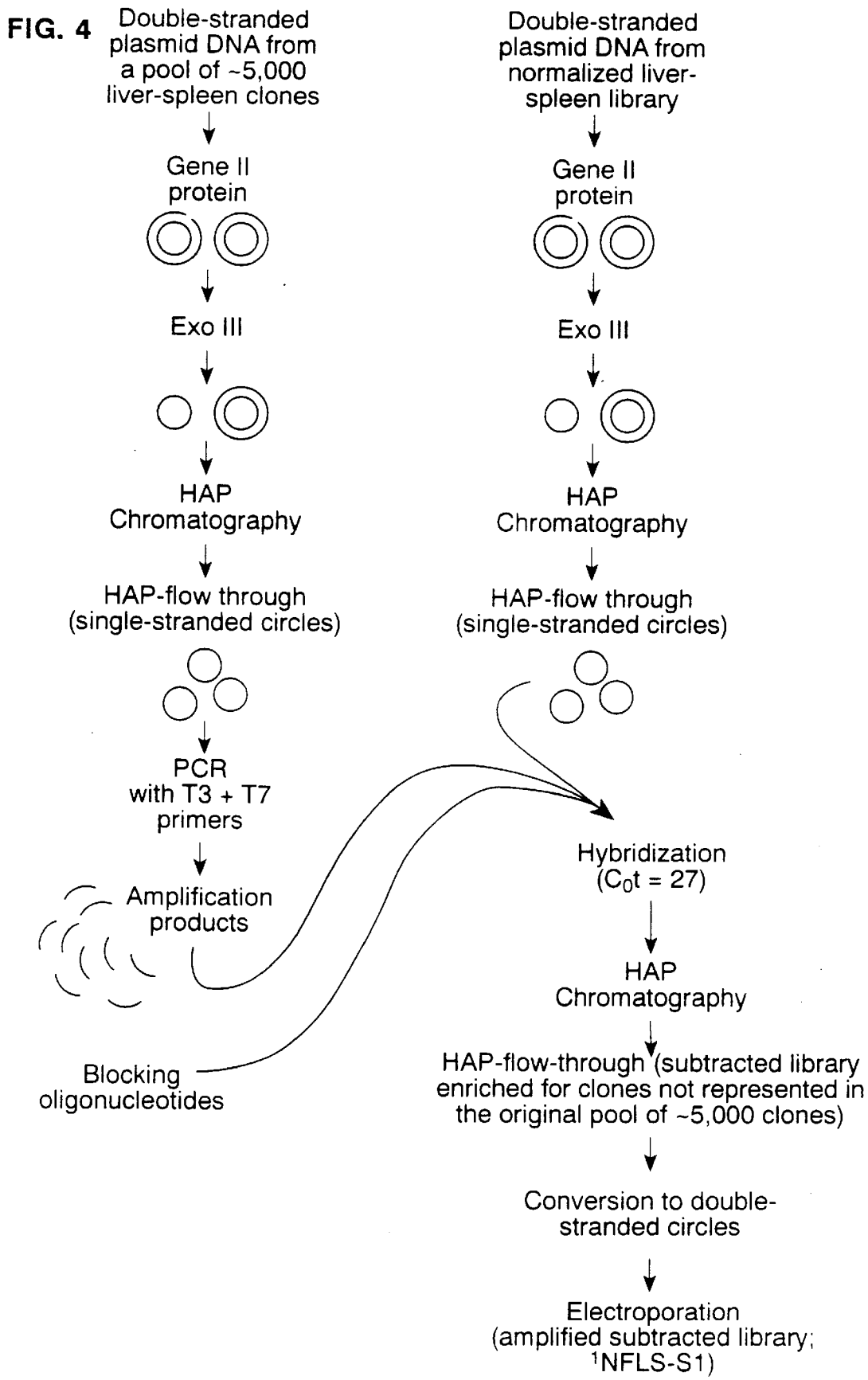
Figure 5A:
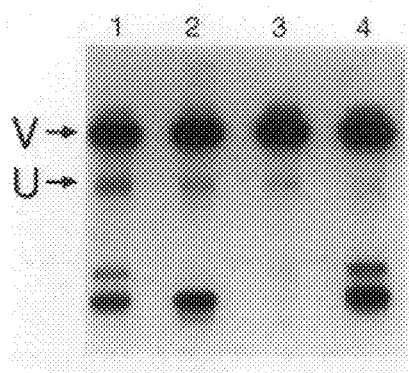
Figure 5B:
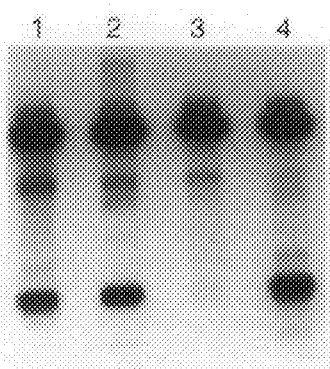
Figure 5C:
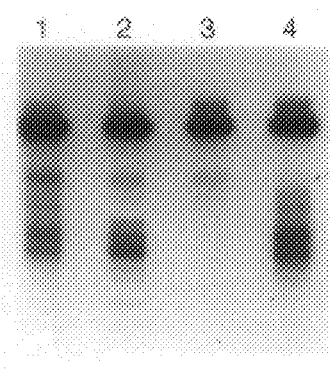
Figure 5D:
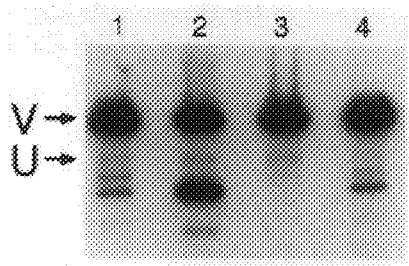
Figure 5E:
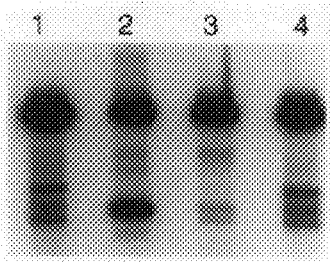

FIG. 4 Diagram of the subtractive hybridization procedure used to generate the $^1$NFLS-S1 library Double-stranded plasmid DNA from a pool of approximately 5,000 I.M.A.G.E. Consortium arrayed cDNA clones derived from the $^1$NFLS library (pool # 1, LLAM 78–90) was converted to single-stranded circles in vitro by the combined action of Gene II and Exonuclease III (Life Technologies). The resulting single-stranded plasmids were HAP-purified and used as template for PCR amplification with T3 and T7 primers. PCR amplified cDNA inserts were purified from excess primers, melted and hybridized with single-stranded circles (prepared in vitro) from the $^1$NFLS library, in the presence of appropriate blocking oligonucleotides. The remaining single-stranded circles were purified by HAP chromatography, converted to double-stranded plasmids, electroporated into DH10B bacteria (Life Technologies) and propagated under ampicillin selection to generate the ($^1$NFLS-S1) subtractive library.

FIGS. 5A–5E Characterization of the $^1$NFLS-S1 subtractive liver-spleen library by Southern hybridization with 5 cDNA probes 0.15 μg Pac I+Eco RI digested plasmid DNA from the fetal liver-spleen library normalized with method 1 ($^1$NFLS;

lane 1), from the pool of approximately 5,000 I.M.A.G.E. Consortium arrayed cDNA clones derived from the [1]NFLS library (pool # 1, LLAM 78–90; lane 2), from the subtractive library generated according to the diagram shown in FIG. 4 ([1]NFLS-S1; lane 3), and from the HAP-Bound fraction obtained during HAP purification of the [1]NFLS-S1 library (see FIG. 4) were electrophoresed, transferred to nylon membranes and hybridized as described in the legend to FIG. 1. The following cDNA probes were used: $\alpha$-Globin (Panel A), $\gamma$-Globin (Panel B), Serum Albumin (Panel C), Unknown cDNA 7 (Panel D; randomly picked from pool # 1, LLAM 78–90) and Unknown cDNA 5 (Panel E; randomly picked from pool # 1, LLAM 78–90). A BLASTN search of the dbEST subdivision of Genbank with 3' ESTs derived from cDNA 7 and cDNA 5 revealed the presence of 33 and 0 corresponding ESTs, respectively, from the [1]NFLS library. All probes were intentionally contaminated with a small amount of vector DNA to enable visualization of vector bands and thus confirm that a similar amount of library DNA was loaded in all lanes. V=vector band; U=residual undigested plasmid.

DETAILED DESCRIPTION OF THE INVENTION

This invention provides a method to normalize a cDNA library comprising: (a) constructing a directionally cloned library containing cDNA inserts wherein the insert is capable of being amplified by polymerase chain reaction; (b) converting a double-stranded cDNA library into single-stranded DNA circles; (c) generating single-stranded nucleic acid molecules complementary to the single-stranded DNA circles converted in step (b) by polymerase chain reaction with appropriate primers; (d) hybridizing the single-stranded DNA circles converted in step (b) with the complementary single-stranded nucleic acid molecules generated in step (c) to produce partial duplexes to an appropriate Cot; and (e) separating the unhybridized single-stranded DNA circles from the hybridized DNA circles, thereby generating a normalized cDNA library.

Methods of constructing a cDNA library are well known in the art. In an embodiment, the cDNA library is constructed in the pT7T3-Pac vector. In another embodiment, the cDNA library is a directional cDNA library. In still another embodiment, the cDNA library is a randomly-primed cDNA library. In a preferred embodiment, the directional cDNA library is generated by using a primer of oligodT stretch. In a more preferred embodiment, the directional cDNA library is generated by using a primer having a rare restriction enzyme recognition site for the first strand cDNA synthesis, upstream of the oligodT stretch. In a most preferred embodiment, the primer contains a specific sequence between the sequence of the rare restriction site and the oligodT stretch.

Rare restriction enzyme sites are well-known in the art. Any restriction enzyme which recognizes a rare restriction recognition site may be used. In an embodiment, a Not I site is used. In another embodiment, a Pac I site is used.

Methods of converting the double-stranded cDNA library into single-stranded DNA circles are well known in the art. As used herein, "single-stranded DNA circles" means single-stranded, circular DNA molecules containing entire sequence of the cDNA inserts and cloning vector of the starting cDNA library.

In an embodiment, the double-stranded cDNA library constructed in a vector capable of being converted into single-stranded DNA circles in vivo is converted into single-stranded DNA circles in vivo. In a preferred embodiment, the double-stranded cDNA library is converted into the single-stranded DNA circles by transforming the cDNA library into bacteria and infecting the transformed bacteria with helper phage capable of converting the double-stranded cDNA library into the single-stranded circles. In a more preferred embodiment, the bacteria used is *Escherichia coli* DH5$\alpha$F' and the helper phage used is M13KO7.

In an embodiment, the double-stranded cDNA library constructed in a vector capable of being converted into single-stranded DNA circles in vitro is converted into single-stranded DNA circles in vitro. In a preferred embodiment, the double-stranded cDNA library is converted into the single-stranded DNA circles by digestion with a site-specific endonuclease and an exonuclease. In a more preferred embodiment, the site-specific endonuclease used is the replication initiator protein of bacteriophage f1, Gene II, and the exonuclease used is Exonuclease III.

This invention also provides a method to normalize a cDNA library comprising: (a) constructing a directionally cloned library containing cDNA inserts; (b) converting a double-stranded cDNA library into single-stranded DNA circles; (c) generating single-stranded nucleic acid molecules complementary to the single-stranded DNA circles converted in step (b) by excising cDNA inserts from the double-stranded cDNA library; purifying the cDNA inserts from cloning vectors; and digesting the cDNA inserts with an exonuclease; (d) hybridizing the single-stranded DNA circles converted in step (b) with the complementary single-stranded nucleic acid molecules generated in step (c) to produce partial duplexes to an appropriate Cot; and (e) separating the unhybridized single-stranded DNA circles from the hybridized DNA circles, thereby generating a normalized cDNA library.

In an embodiment, the double-stranded cDNA library is converted into the single-stranded DNA circles in vitro. In another embodiment, the double-stranded cDNA library is converted into the single-stranded DNA circles in vivo. In a preferred embodiment, the double-stranded cDNA library is converted into the single-stranded circles by treating the double-stranded cDNA library with an exonuclease. In a more preferred embodiment, the exonuclease used is Exonuclease III. The methodology of conversion of double-stranded cDNA into the single-stranded circles by using an endonuclease (Gene II) combined with an exonuclease (Exonuclease III) may be achieved by using commercially available kits such as one manufactured by Life Technologies. In a preferred embodiment, the single-stranded DNA circles are separated from the unconverted double-stranded cDNA library. In a most preferred embodiment, the single-stranded DNA circles are separated from the unconverted double-stranded cDNA library by hydroxyapatite column chromatography.

As used herein, "single-stranded nucleic acid molecules complementary to the single-stranded DNA circles" means single-stranded DNA or RNA molecules containing sequence complementary to the sequence of the entire or any portions of the single-stranded DNA circles. The single-stranded nucleic acid molecules complementary to the single-stranded DNA circles are not generated by annealing the single-stranded DNA circles converted to an appropriate primer and performing controlled extension reactions with an appropriate polymerase, i.e., are not fragments complementary only to the 3' noncoding sequence of the single-stranded DNA circles, and are not RNA fragments complementary to the single-stranded DNA circles converted in step (a) by in vitro transcription of the double-stranded cDNA library.

Methods of generating single-stranded nucleic acid molecules complementary to the single-stranded DNA circles are well known in the art. In an embodiment, the single-stranded DNA circles generated in step (c) comprise the 5' halves of all cDNA inserts of the double-stranded cDNA library used in step (a).

In a separate embodiment, the single-stranded nucleic acid molecules generated in step (c) span the entire length of the cDNA inserts. In a further embodiment, the single-stranded nucleic acid molecules are generated by PCR amplification of all cDNA inserts of the cDNA library. In a separate embodiment the PCR products may be separated from PCR primers. In a preferred embodiment, the single-stranded nucleic acid molecules are generated by PCR amplification of all cDNA inserts of the cDNA library, using the single-stranded circles converted in step (b) as a PCR template, and the PCR products are separated from PCR primers. In a more preferred embodiment, oligonucleotides complementary to sequences that immediately flank the cloning sites of cDNA inserts in the cDNA library are used as PCR primers. In a most preferred embodiment, oligonucleotides complementary to T3 and T7 promoters are used as PCR primers.

Conditions under which the single-stranded DNA circles hybridize with complementary single-stranded nucleic acid molecules to produce partial duplexes to an appropriate Cot have been known in the art. In an embodiment, the complementary nucleic acid molecules are in excess of the single-stranded DNA circles. In another embodiment, the complementary nucleic acid molecules are in excess of the single-stranded circles by at least twenty times. In a preferred embodiment, the complementary nucleic acid molecules and the single-stranded DNA circles are hybridized to a Cot of about five to twenty in the presence of a vast excess of blocking oligonucleotides. In a more preferred embodiment, the complementary nucleic acid molecules and the single-stranded circles are hybridized under conditions similar to that used for hydroxyapatite column chromatography. In a most preferred embodiment, the complementary nucleic acid molecules and the single-stranded DNA circles are hybridized in a solution comprising 0.12M NaCl-50% formamide-1% SDS-5 mM EDTA pH 8.0 at 30° C. for an appropriate amount of time which corresponds to a Cot about 5. In an embodiment the amount of time is 24 hours.

Methods of separating the unhybridized single-stranded DNA circles from the hybridized DNA circles are known in the art. In an embodiment, the hybridized DNA circles and the unhybridized single-stranded DNA circles are separated by hydroxyapatite column chromatography.

This invention also provides the above methods which further comprise a method of introducing the unhybridized or hybridized single-stranded DNA circles into host cells. In a preferred embodiment, the unhybridized single-stranded DNA circles are converted into double-stranded DNA circles before the introduction into the hosts. In a preferred embodiment a mini-library for abundant cDNAs is generated by introducing the hybridized single-stranded DNA circles into host cells. In a preferred embodiment, the hybridized single-stranded DNA circles are converted into double-stranded DNA circles before the introduction into the hosts.

This invention further provides normalized cDNA libraries which are generated by the above-described methods. In an embodiment, the cDNA library is derived from human fetal liver-spleen. In another embodiment, the cDNA library is derived from human 8–9W placenta. In another embodiment, the cDNA library is derived from human melanocytes. In another embodiment, the cDNA library is derived from human fetal heart. In another embodiment, the cDNA library is derived from human parathyroid adenoma. In another embodiment, the cDNA library is derived from human senescent fibroblast. In another embodiment, the cDNA library is derived from human multiple sclerosis plaques. In another embodiment, the cDNA library is derived from human fetal lung. In another embodiment, the cDNA library is derived from 19.5 dpc mouse embryo. In another embodiment, the cDNA library is derived from 17.5 dpc mouse embryo. In another embodiment, the cDNA library is derived from 13.5–14.5 dpc mouse embryos. In another embodiment, the cDNA library is derived from rat heart. In another embodiment, the cDNA library is derived from rat kidney. In another embodiment, the cDNA library is derived from 8 week adult Schistosome.

This invention further provides a method to construct a subtractive cDNA library comprising: (a) converting of a double-stranded cDNA library into single-stranded DNA circles; (b) treating a pool of double-stranded DNAs which are to be eliminated from the subtractive cDNA library with a site-specific endonuclease and an exonuclease to generate single-stranded DNA molecules; (c) separating the single-stranded DNA molecules from the double-stranded DNAs; (d) amplifying the separated single-stranded DNA molecules by PCR; (e) hybridizing the single-stranded DNA circles converted in step (a) with single-stranded DNA molecules generated in step (b) to produce partial duplexes to an appropriate Cot; and (f) separating the unhybridized single-stranded DNA circles from the hybridized DNA circles, thereby generating a subtractive cDNA library.

In an embodiment, the double-stranded cDNA library is converted into the single-stranded DNA circles by treating the double-stranded cDNA library with a site-specific endonuclease and an exonuclease. In a preferred embodiment, the site-specific endonuclease used is the replication initiator protein of bacteriophage f1 (Gene II) and the exonuclease used is Exonuclease III. In a preferred embodiment, the single-stranded DNA circles are separated from the unconverted double-stranded cDNA library. In a more preferred embodiment, the single-stranded DNA circles are separated from the unconverted double-stranded cDNA library by hydroxyapatite column chromatography.

In a separate embodiment, the pool of double-stranded DNAs which are to be eliminated from the subtractive cDNA library are treated with the replication initiator protein of bacteriophage f1 (Gene II) and the exonuclease used is Exonuclease III. In a preferred embodiment, the single-stranded DNA molecules are separated from the unconverted double-stranded cDNA pool by hydroxyapatite column chromatography. In a more preferred embodiment, oligonucleotides complementary to sequences that immediately flank the cloning sites of the double-stranded DNA pool are used as PCR primers to amplify the single-stranded DNA molecules. In a most preferred embodiment, oligonucleotides complementary to T3 and T7 promoters are used as PCR primers.

In a separate embodiment, the single-stranded DNA molecules are in excess of the single-stranded DNA circles. In a preferred embodiment, the single-stranded DNA molecules and the single-stranded DNA circles are hybridized to a Cot of about five to fifty in the presence of a vast excess of blocking oligonucleotides. In a more preferred embodiment, the single-stranded DNA molecules and the single-stranded DNA circles are hybridized under conditions similar to that used for hydroxyapatite column chromatography.

In a separate embodiment, the hybridized DNA circles and the unhybridized single-stranded DNA circles are separated by hydroxyapatite column chromatography.

This invention also provides the above methods which further comprise introducing the unhybridized single-stranded DNA circles (subtractive cDNA libraries) into host cells. In another embodiment, the unhybridized single-stranded DNA circles are converted into double-stranded DNA circles before the introduction into the hosts.

This invention further provides subtractive cDNA libraries which are generated by the above-described methods. In an embodiment, a subtractive and normalized cDNA library is generated, wherein the starting cDNA library is a normalized cDNA library. In another embodiment, a subtractive and normalized cDNA library is generated wherein the double-stranded DNAs to be eliminated from the subtractive library comprise a pool of 3,992 clones with I.M.A.G.E. Consortium Identification Numbers 66696–67079 and 108168–112775 derived from the normalized fetal liver-spleen library ($^1$NFLS).

The invention will be better understood by reference to the Experimental Details which follow, but those skilled in SEQ ID NO. 3 was used to prime the synthesis of first-strand fetal liver-spleen cDNA. Double-stranded cDNAs were size selected by gel filtration over a long (64 cm) and narrow (0.2 cm diameter) Bio-Gel A-50 m (Bio-Rad, 100–200 mesh) column, and ligated to a 500–1,000 fold molar excess of adapters. Infant brain cDNAs were ligated to Hind III adapters, digested with Not I, size selected over a second Bio-Gel column, and directionally cloned into the Not I and Hind III sites of the Lafmid BA vector (Soares et al. 1994). Fetal liver-spleen cDNAs were ligated to Eco RI adapters (Pharmacia), size selected as above, digested with Pac I and directionally cloned into the Pac I and Eco RI sites of the pT7T3-Pac vector. All other cDNAs were ligated to Eco RI adapters (Pharmacia), size selected as above, digested with Not I and directionally cloned into the Not I and Eco RI sites of the pT7T3-Pac vector. pT7T3-Pac is essentially the same as pT7T318D (Pharmacia) with a modified polylinker. Following is the sequence of the pT7T3-Pac polylinker (in upper case) and flanking sequences (in lower case):

5' caccccaggctttacactttatgcttccggctcgtatgttgtgtggaattgtgagc ggataacaatttcacacaggaaacagctatgacatgattacgaatttaatacgactca
M13 Reverse Sequencing Primer                    T7 Promoter ctatagggaatttGGCCCTCGAGGCCAAGAATTCCCGACTACGTAGTCGGGGATCCGT
            Sfi I         Eco RI         Sna BI        Bam HI CTTAATTAAGCGGCCGCAAGCTTattcccttagtgagggttaattttagcttggcac
  Pac I    Not I   Hind III    T3 Promoter tggccgtcgttttacaacgtcgtgactgggaaaaccctggcgttacccaacttaatcg
                        M13 Sequencing Primer ccttgcag 3' SEQ ID NO. 4.

the art will readily appreciate that the specific experiments detailed here are only illustrative, and are not meant to limit the invention as described herein, which is defined by the claims which follow thereafter.

Experimental Methods

Construction of directionally cloned cDNA libraries

Poly(A)+RNA was purified from total cellular RNA (except for senescent fibroblasts from which cytoplasmic RNA was isolated) using the Oligotex mRNA kit (Qiagen) according to the manufacturer's instructions, except that two rounds of purification were performed. cDNA library construction was essentially as described before (Adams et al. 1993b; Soares 1994). Typically, 1 µg poly(A)+RNA was annealed at 37° C. with a two-fold mass excess of a Not I-tag- [dT]$_{18}$ primer (or Pac I-tag-[dT]$_{18}$ in the case of the liver-spleen library) and reverse transcribed at 37° C. with Superscript Reverse Transcriptase (Life Technologies). Alternatively Poly(A)+RNA was annealed at 45° C. with a four-fold mass excess of a Not I-tag-[dT]$_{25}$ primer and reverse transcribed at 45° C. The "tag" is a sequence of 2–6 nucleotides which is unique for each library and thus serves as an identifier (see Table 1).

With the exception of infant brain, fetal liver-spleen and term placenta, all other first-strand cDNA syntheses were primed with the following oligonucleotide: TGTTACCAATCTGAAGTGGGAGCGGCCGC-tag-[dT]$_{18}$ or 25 SEQ ID NO. 1. The oligonucleotide AACTGGAAGAATTCGCGGCCGCAGGAA[dT]$_{18}$ SEQ ID NO. 2 (Pharmacia) was used to prime both infant brain and term placenta first-strand cDNA syntheses. The oligonucleotide AACTGGAAGAATTAATTAAAGATCT[dT]$_{18}$ Production of purified covalently-closed single-stranded library DNA in vitro Double-stranded phagemid DNA was converted to single-stranded circles by the combined action of Gene II (phage F1 endonuclease) and E. coli Exonuclease III enzymes, as per the manufacturer's instructions (Life Technologies; Cat. No. 10356-020). The resulting single-stranded circular DNA was purified from the remaining double-stranded plasmids by HAP chromatography (Bio-Rad) as previously described (Soares et al., 1994). The replication initiator protein of bacteriophage f1 (Gene II) is a site-specific endonuclease that binds to the f1 origin in phagemid vectors and nicks the viral strand of the supercoiled DNA (Johnston et al. 1985; Rasched and Oberer 1986). The nicked strand is then digested from its 3' end with Exonuclease III (Hoheisel 1993) to generate single-stranded circles. Purification of the resulting single-stranded circles over HAP is necessary because the conversion of supercoiled to relaxed plasmids by Gene II is never complete. The Gene II reaction was performed for 1 h at 30° C. and typically contained 4 µg supercoiled plasmid library DNA, 1 µl Gene II (Life Technologies) and 2 µl 10× Gene II buffer (Life Technologies) in a total volume of 20 µl. The Gene II protein was heat inactivated for 5 min at 65° C., the reaction mixture was chilled on ice, 2 µl Exonuclease III (Life Technologies, Cat. No. 18013-011, 65 units/µl) was added and the reaction was incubated for 30 min at 37° C. Gene II and Exonuclease III were then digested with Proteinase K (Boehringer Mannheim) for 15 min at 50° C. in a 100 µl reaction containing 10 mnM Tris, pH7.8-5 mM EDTA-0.5% SDS-136 µg Proteinase K. After extraction with equal volume of phenol:chloroform:isoamyl alcohol (25:24:1), library DNA was ethanol precipitated and digested with Pvu II for 2 h at 37° C. This was done to convert the remaining supercoiled plasmids into linear DNA molecules and thereby improve their bindability to HAP under these conditions. Note that Pvu II does not cleave single-stranded circles and that there are two Pvu II sites in the vector. The reaction was diluted with 2 ml loading buffer (0.12M sodium phosphate buffer, pH6.8-10 mM EDTA-1% SDS), and purified by HAP chromatography at 60° C., using a column preequilibrated with the same buffer (1 ml bed volume; 0.4 g of HAP). After a 6 ml wash with loading buffer, this volume was combined with the flow through fraction, and the sample was extracted twice with water-saturated 2-butanol, once with dry 2-butanol, and once with water-saturated ether (3 volumes per extraction). Residual ether was blown off by vacuum and the sample was desalted by passage through a Nensorb column (DuPont/NEN) according to the manufacturer's specifications, concentrated down to about 0.35 ml and ethanol precipitated. Note that Gene II-Exonuclease III-prepared single-stranded DNA is in the opposite polarity to single-stranded DNA generated by in vivo phagemid production.

Production of purified covalently-closed single-stranded library DNA in vivo

Plasmid DNA from the starting library was electroporated into *Escherichia coli* DH5αF' bacteria, and the culture was grown under ampicillin selection at 37° C. to an $OD_{600}$ of 0.2, superinfected with a 10–20-fold excess of the helper phage M13KO7 (Pharmacia), and harvested after 4 h for preparation of single-stranded plasmids, as described (Vieira and Messing 1987).

Conversion of single-stranded circles to double-stranded plasmids

Single-stranded circles (<50 nanograms) were ethanol precipitated and resuspended in 11 µl water. 4 µl 5×Sequenase buffer (USB) and 1 µl primer (1 µg) were added and the mixture was incubated at 65° C. for 5 min and then at 37° C. for 3 min. 1 µl Sequenase version 2.0 (USB), 1 µl 0.1M DTT and 2 µl mixed dNTP stock (a solution containing each deoxynucleotide at a final concentration of 10 mM) were added and the reaction was incubated at 37° C. for 30 min. The total volume was taken up to 100 µl with TE and the reaction was extracted once with phenol:chloroform:isoamyl alcohol (25:24:1). Plasmid DNA was ethanol precipitated and dissolved in 3 µl TE. The following oligonucleotides were used for this primer extension reaction: (1) M13 Reverse Sequencing Primer [5' AGCG-GATAACAATTTCACACAGGA 3']SEQ ID NO. 5, which is complementary to single-stranded prepared in vitro; (2) Oligo-Amp [5' GACTGGTGAGTACTCAACCAAGTC 3'], SEQ ID NO. 6 which is complementary to the ampicillin resistance gene of single-stranded pT7T3-Pac or Lafmid BA plasmids prepared in vivo.

In vitro synthesis of library RNA

2–5 µg of double-stranded plasmid DNA from either the starting library (see Methods 2-1 and 2-2 below) or the mini-library of abundant cDNAs (see Method 2-3 below) was linearized with either Pac I (NEB) or Not I (NEB) and used as template for synthesis of RNA with RiboMax Large Scale RNA Production Systems T7 or T3 (Promega), according to the manufacturer's instructions. After treatment with RNAse free DNAse I (Promega), to digest away the plasmid DNA template, the RNA was used for hybridization as described below. It should be noted that RNA synthesized with T7 RNA Polymerase is in the message-like orientation and it is complementary to the single-stranded circles produced in vitro. On the other hand, RNA synthesized with T3 RNA Polymerase is in the antimessage orientation and it is complementary to single-stranded circles produced in vivo.

Normalization Method 1

The procedure used for construction of the normalized human infant brain ([1]NIB) library (here designated as Method 1) has been previously described (Soares et al. 1994). Method 1, with minor modifications, was also applied to construct the normalized human fetal liver-spleen cDNA library ([1]NFLS). To synthesize a partial second strand of about 200 nt by limited extension, a 100 µl reaction mixture containing 5 µl 0.5 µg/µl Pvu II-digested, HAP- and gel-purified single-stranded plasmid DNA from the fetal liver-spleen starting library, 7 µl 10 nanograms/µl oligo [dT]$_{12-18}$ (Pharmacia), 10 µl 10×Primer Extension Buffer (0.3M Tris pH7.5-0.5M NaCl-0.15M $MgCl_2$), 10 µl 0.1M DTT, 10 µl mixed dNTP stock (a solution containing each one of the four deoxynucleotides at a final concentration of 10 mM), 25 µl mixed ddNTP stock (a solution containing each dideoxy A, C and G at a final concentration of 25 mM), 5 µl 800 Ci/mmole [α-$^{32}$P]dCTP and 20.5 µl water was incubated at 60° C. for 5 min, at 50° C. for 15 min and at 37° C. for 2 min. 7.5 µl 5 units/µl Klenow enzyme (USB) was added and the reaction was incubated at 37° C. for 30 min. The reaction was extracted with phenol:chloroform:isoamyl alcohol (25:24:1), 5 µg melted and sheared salmon sperm DNA was added, and the partially double-stranded plasmids were purified from the remaining single-stranded circles (unprimed molecules, as well as clones derived from mRNAs with an internal Pac I site which therefore do not contain an oligo[dA] tail at the 3' end) by HAP chromatography. The HAP-bound fraction containing the partially double-stranded plasmids was eluted with 6 ml 0.4M sodium phosphate buffer, pH6.8-10 mM EDTA -1% SDS and plasmid DNA was desalted as described before (Soares et al. 1994) and ethanol precipitated. The DNA (173 nanograms) was resuspended in 2.5 µl deionized formamide and melted at 80° C. for 3 min under 10 µl mineral oil. 1 µl 5 µg/µl oligo[dT]$_{12-18}$ (used to block the tails) was added and the mixture was heated at 80° C. for 1 min. 0.5 µl 5M NaCl, 0.5 µl 10×TE and 0.5 µl water were added and the reassociation reaction was incubated at 42° C. for 0.6 h (calculated $C_0t=0.5$). The remaining single-stranded circles were purified over HAP (flow-through fraction) and subsequently subjected to a second cycle of the normalization procedure as described above, except that reassociation was conducted for 24 h (calculated $C_0t=20$). The remaining single-stranded circles (normalized library; [1]NFLS) were purified over HAP, converted to double-stranded plasmids, electroporated into DH10B bacteria and propagated under ampicillin selection.

Normalization Methods 2-1, 2-2 and 2-3

Method 2 is a reassociation kinetics-based approach involving hybridization of in vitro synthesized RNA (the driver) derived either from the entire library (methods 2-1 and 2-2; see FIG. 2), or from a mini-library enriched for abundant cDNAs (method 2-3; see FIG. 2), with the whole starting library in the form of single-stranded circles (the tracer). The remaining single-stranded circles (normalized library) are purified by HAP chromatography (HAP flow-through fraction), converted to double-stranded plasmids for improvement of electroporation efficiency, electroporated into DH10B bacteria (Life Technologies), and propagated under ampicillin selection. A number of normalized cDNA libraries were constructed with these methods using both single-stranded plasmids prepared in vivo and in vitro (see Table 1). In all three variants, the driver was first pre-annealed with a pair of oligonucleotides to block both 5' and 3' vector sequences as follows: 0.5 µl (10 µg) of each oligonucleotide, 1 μl RNA (5.0 μg in Methods 2-1 and 2-3; 0.5 μg in Method 2-2), and 4.0 μl deionized formamide were heated for 3 min at 80° C. under 10 μl mineral oil and quickly chilled on ice. 0.8 μl 10×hybridization buffer [0.4M Pipes pH 6.4-4M NaCl-10 mM EDTA in Methods 2-1 and 2-3; 0.4M Pipes pH 6.4-1.2M NaCl-10 mM EDTA-1% SDS in Method 2-2], 0.5 μl RNAsin (Boehringer Mannnheim) and 0.7 μl water were added and the mixture (total volume of 8 μl) was incubated overnight at 42° C. (Methods 2-1 and 2-3) or 30° C. (Method 2-2). In another tube, 2.5 μl (50 nanograms) single-stranded library DNA in deionized formamide was heated for 3 min at 80° C. under mineral oil, 0.5 μl 10×hybridization buffer and 2.0 μl water were added and the mixture was transferred to the tube containing the pre-annealed RNA. Hybridization (13 μl reaction) was performed at 42° C. (Method 2-1: $C_0t$ of 5–10; Method 2-3: $C_0t$ of 100–200) or at 30° C. (Method 2-2: $C_0t$ of 5–10). The driver, rather than the tracer, was blocked because otherwise the latter would, to some extent, bind to HAP during purification. The plasmid mini-library enriched for abundant cDNAs that served as template for the synthesis of RNA used as driver in Method 2-3 was prepared from the HAP bound fraction obtained during purification of the normalized library in Method 2-1. Different pairs of blocking oligonucleotides were used depending on whether the RNA was synthesized with T3 or T7 RNA Polymerases, as specified below:

(a) to block RNA synthesized with T3 RNA Polymerase which was used in hybridizations with single-stranded plasmids prepared in vivo: 5' $_{19}$AGGGCGGCCGCAAGCTTAT-TCCCTTTAGTGAGGGTTAAT 3' SEQ ID NO. 7 (this oligonucleotide was used to block 5' vector sequences of all but the human fetal liver-spleen library RNA); 5' $_{19}$AGATCTTTAATTAAGCGGCCGCAAGCT-TATTCCCTTTAGTGAGGGTTAAT 3' SEQ ID NO. 8 (this oligonucleotide was used to block 5' vector sequences of the human fetal liver-spleen library RNA); 5' AGGCCAA-GAATTCGGCACGAG 3' SEQ ID NO. 9 (this oligonucleotide was used to block 3' vector sequences);

(b) to block RNA synthesized with T7 RNA Polymerase which was used in hybridizations with single-stranded plasmids prepared in vitro: 5' CCTCGTGCCGAATTCTTGGC-CTCGAGGGCCAAATTCCC 3' SEQ ID NO. 10 (this oligonucleotide was used to block 5' vector sequences). The oligonucleotide used to prime the synthesis of first-strand cDNA was also used to block 3' vector sequences.

Normalization Method 3

Method 3, which was used to generate the normalized library from multiple sclerosis plaques ($^2$NbHMSP), is a reassociation kinetics based approach involving hybridization ($C_0t$ of 20–25) of a 20-fold excess of Exonuclease III-digested cDNA inserts excised from a plasmid DNA preparation of the starting library with the library itself in the form of single-stranded circles, followed by HAP-purification of the remaining single-stranded plasmids, conversion to double-strands and electroporation into bacteria. 5 μg double-stranded plasmid DNA from the starting library was doubly digested with Not I and Eco RI, the excised cDNA inserts were separated from the cloning vector by agarose gel electrophoresis, and the DNA was purified using beta-agarase (NEB) according to the manufacturer's instructions. 0.6 μg gel purified double-stranded cDNA inserts in 47.5 μl TE was digested with Exonuclease III at 37° C. for 30 min in a 60 μl reaction containing 6 μl 10×Exonuclease III buffer (0.5M Tris pH8.0-50 mM MgCl2), 0.6 μl 0.1M DTT, 2.9 μl water and 3 μl 65 units/μl Exonuclease III (Life Technologies). The Exonuclease was then digested with 136 μg Proteinase K (Boehringer Mannheim) at 50° C. for 15 min in a 100 μl reaction containing 10 mM Tris, pH 7.8-5 mM EDTA-0.5% SDS. After two extractions with phenol:chloroform:isoamyl alcohol (25:24:1), the resulting non complementary single-stranded DNA (total estimated amount of 0.3 μg) was ethanol precipitated and resuspended in 1 μl TE. A 5 μl hybridization reaction was then set up as follows: 1 μl Exonuclease III-digested cDNA inserts (an estimated amount of 150 nanograms of single-stranded DNA), and 50 nanograms single-stranded plasmid DNA from the starting multiple sclerosis plaques library (prepared in vitro) in 2.5 μl deionized formamide were mixed and heated at 80° C. for 3 min under 10 μl mineral oil. 0.5 μl (10 μg) of a blocking oligonucleotide [5' CCTCGTGCCGAAT-TCTTGGCCTCGAGGGCCAAATTCCCTAT-AGTGAGTCGTATTA 3'], SEQ ID NO: 11 0.5 μl 5M NaCl, and 0.5 μl 10×TE were added and the mixture was incubated at 42° C. for 41 h (calculated $C_0t$ of 23). The remaining single-stranded plasmids were purified by HAP chromatography, converted to double-stranded plasmids, and electroporated into DH10B bacteria (Life Technologies) as described above.

Normalization Method 4

This is a reassociation kinetics based approach involving hybridization of a 20-fold excess of cDNA inserts generated by the Polymerase Chain Reaction (PCR) with the library itself in the form of single-stranded circles, followed by HAP-purification of the remaining single-stranded plasmids, conversion to double-strands, electroporation into DH10B bacteria and amplification under ampicillin selection. PCR amplification of cDNA inserts was performed using the Expand High Fidelity PCR System (Boehringer Mannheim) according to the manufacturer's instructions. This PCR system is composed of an enzyme mixture containing thermostable Taq DNA and Pwo DNA Polymerases (Barnes 1994). 1 μl (2.5–5.0 nanograms) DNA template [double-stranded plasmids (fetal lung, parathyroid adenoma, senescent fibroblasts), or single-stranded circles prepared in vitro (fetal heart, $^{14}$Nb$^2$HFLS20W-fetal liver-spleen, and all mouse, rat and Schistosome libraries listed in Table 1)] was mixed with 2 μl dNTP stock (a solution containing each deoxynucleotide at a final concentration of 10 mM; the final concentration of each dNTP in the reaction is 200 μM), 5 μl of a 20 μM solution of T7 Primer [5' TAATACGACTCAC-TATAGGG 3'], SEQ ID NO: 12 5 μl of a 20 μM solution of T3 Primer [5' ATTAACCCTCACTAAAGGGA 3'], SEQ ID NO: 13 10 μl 10×Expand High Fidelity buffer, 0.75 μl Expand High Fidelity enzyme mix (2.6 units) and 76.25 μl water. 50 μl mineral oil was added and the reaction mixture was subjected to the following amplification cycle conditions in a Perkin Elmer Thermocycler: (a) 7 min while ramping up from room temperature to 94° C., (b) 20 cycles of 1 min at 94° C., 2 min at 55° C. and 3 min at 72° C., and (c) 7 min at 72° C. PCR-amplified fragments were purified using the High Pure PCR Product Purification Kit (Boehringer Mannheim) exactly as instructed by the manufacturer. The purified PCR product was ethanol precipitated and dissolved in 5 μl TE. 1.5 μl (0.5 μg) PCR products was mixed with 5 μl (50 nanograms) library DNA (single-stranded circles prepared in vitro) in deionized formamide, 0.5 μl (10 μg) 5' blocking oligo AV-1 [5' CCTCGTGC-CGAATTCTTGGCCTCGAGGGCCAAATTC-CCTATAGTGAGTCGTATTA 3'], SEQ ID NO: 14 0.5 μl (10 μg) 3' blocking oligo AR [5' ATTAACCCTCAC-TAAAGGGAATAAGCTTGCGGCCGCT$_{20}$ 3'; SEQ ID NO: 15 used for all but the fetal liver-spleen library], or alternatively 0.5 μl (10 μg) 3' blocking oligo AV-2 [5'

ATTAACCCTCACTAAAGGGAATAAGCT-
TGCGGCCGCTTAATTAAAGATCT$_{19}$ 3'; SEQ ID NO: 16
used only for the fetal liver-spleen library), and this mixture
was heated at 80° C. for 3 min under 10 μl of mineral oil. 1
μl 10×buffer-A [1.2M NaCl-0.1M Tris pH8.0-50 mM
EDTA; used for fetal lung, fetal heart, parathyroid adenoma,
senescent fibroblasts and 19.5 dpc mouse embryo], or alter-
natively 1 μl 10×buffer-B [1.2M NaCl-0.1M Tris pH8.0-50
mM EDTA-10% SDS; used for $^{14}$Nb$^2$HFLS20W-fetal liver-
spleen, 17.5 dpc mouse embryo, 13.5–14.5 dpc mouse
embryo, rat heart, rat kidney, and 8 week Schistosome], and
1.5 μl water were added and the hybridization was per-
formed at 30° C. for 24 h (calculated $C_0t$ of approximately
5). The remaining single-stranded circles were purified by
HAP chromatography, converted to double-strands and elec-
troporated into DH10B (Life Technologies) bacteria, as
described above.

Subtractive hybridization

Double-stranded plasmid DNA from a pool of 4,992
clones grown individually in 384 well plates (I.M.A.G.E.
Consortium plates LLAM 78–90, Identification numbers
66696–67079 and 108168–112775) derived from the nor-
malized fetal liver-spleen library ($^1$NFLS) was prepared
using the Qiagen Midiprep kit according to the manufactur-
er's instructions, and converted to single-stranded circles in
vitro, as described above. Single-stranded circles were puri-
fied by HAP chromatography and used as template for PCR
amplification with T7 and T3 primers, as described above.
1.5 μg of PCR amplified cDNA inserts from the LLAM
78–90 pool (in 4 μl deionized formamide) was mixed with
50 nanograms of single-stranded circles from the $^1$NFLS
library (in 2 μl deionized formamide), 2.1 μl (42 μg) 5'
blocking oligo AV-1 and 2.1 μl (42 μg) 3' blocking oligo
AV-2. 10 μl mineral oil was added and the mixture was
heated at 80° C. for 3 min. 1.2 μl 10×buffer-B and 0.6 μl
water were added and the hybridization was performed at
30° C. for 48 h (calculated $C_0t$=27). The remaining single-
stranded circles were purified over HAP, converted to
double-strands, electroporated into DH10B bacteria and
propagated under ampicillin selection to generate the sub-
tractive liver-spleen library (1NFLS-S1). HAP-bound DNA
was also processed and purified for use in control experi-
ments.

Experimental Results

While attempting to improve the representation of full-
length cDNAs in normalized libraries, four methods were
developed and constructed over thirty five libraries, most of
which are described here. A list comprising fifteen human,
three mouse, two rat and one Schistosome libraries with
their respective names, number of recombinants, sequence
tags and methods used for normalization and preparation of
single-stranded plasmids is shown in Table 1.

Extensive characterization of two normalized libraries
($^1$NIB and $^1$NFLS) constructed according to our previously
described procedure (Soares et al. 1994; here designated as
Method 1) confirmed our original observations that a great
extent of normalization can be achieved with this method for
most cDNA species (e.g., compare lanes 9 and 10 in panels
M, N, O and P in FIG. 1). It is noteworthy that the frequency
of cDNA 122 (used as probe in panel P) was increased with
normalization from <0.0006% in the starting library to
0.007% in the $^1$NIB library (Soares et al., 1994). However,
Southern hybridization of starting and normalized libraries
with a battery of cDNA probes revealed that on occasion
truncated clones were favored over their full-length coun-
terparts during the process. This was first observed when
Southern blots of Not I+Hind III digested plasmid DNA
from starting and normalized infant brain libraries were
hybridized with a cDNA probe for mitochondrial 16S rRNA
(see FIG. 1, Panel L, lanes 9 and 10). Not only was the
frequency of these mitochondrial cDNA clones reduced
effectively during the process of normalization (frequency of
occurrence in starting and normalized infant brain libraries
was 1.4% and 1.0%, respectively), but also the length of the
hybridizing cDNAs was noticeably smaller in the normal-
ized library. Comparative sequence analysis (not shown) of
a number of hybridizing mitochondrial 16S rRNA clones
from both starting and normalized libraries revealed that
whereas the 3' end of most cDNAs derived from the starting
library corresponded to the bona fide 3' end of the 16S
rRNA, the 3' end of the majority of the cDNAs isolated from
the normalized library corresponded to sequences further
upstream on the 16S rRNA. The occurrence of such 3'
truncations was also documented by sequence analysis (not
shown) for serum albumin cDNAs in the fetal liver-spleen
library (see FIG. 1, Panels D and E, lanes 4 and 6).

Figure 1A:
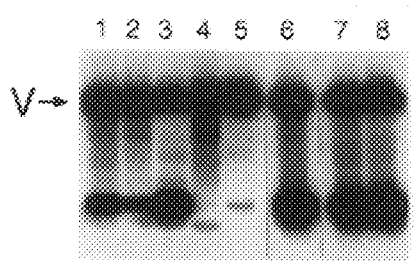
FIGS. 1A–1P Comparative analysis of starting and normalized cDNA libraries by Southern hybridization with 14 cDNA probes 0.015 μg Pac I+Eco RI digested plasmid DNA from the starting fetal liver-spleen library (lane 6), from the normalized fetal liver-spleen libraries constructed according to method 2-1 (lane 1), method 2-3 (lane 2), method 2-2 (lane 3), method 1 (lane 4), method 4 (lane 5), and from the liver-spleen mini-libraries enriched for abundant cDNAs (HAP-Bound fractions) generated with method 2-1 (lane 7) and method 4 (lane 8) were electrophoresed on 1% agarose gels, transferred to nylon membranes (GeneScreenPlus; DuPont/NEN) and hybridized at 42° C. in 50% formamide-5×Denhardt's solution-0.75M NaCl-0.15M Tris pH7.5 -0.1M Sodium Phosphate-0.1% Sodium Pyrophosphate-2% SDS containing sheared and denatured salmon sperm DNA at 100 μg/ml. Similarly, 0.05 μg Not I+Hind III digested plasmid DNA from the starting (IB; lane 9) and normalized ($^1$NIB; lane 10; method 1) infant brain libraries (Soares et al., 1994) were electrophoresed, transferred and hybridized as described above. Radioactive probes were prepared by random primed synthesis using the Prime-it II kit (Stratagene). The following probes were used: α-Globin (Panel A), β-Globin (Panel B), γ-Globin (Panel C), Serum Albumin (Panel D, shorter exposure; Panel E, longer exposure), Acidic Ribosomal Phosphoprotein PO (Panel F), H19 RNA (Panel G, shorter exposure; Panel H, longer exposure), Apolipoprotein A (Panel I), Angiotensinogen (Panel J), Unknown cDNA 8 (Panel K), Mitochondrial 16S rRNA (Panel L), α-Tubulin (Panel M), Myelin Basic Protein (Panel N), Secretogranin (Panel O) and Unknown cDNA 122 (Panel P). All probes were intentionally contaminated with a small amount of vector DNA to enable visualization of vector bands and thus confirm that a similar amount of library DNA was loaded in all lanes. V=vector band, which is released from the cDNA inserts by double digestion with the restriction enzymes specified above.
Figure 1B:
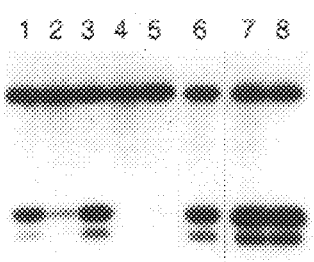
Figure 1C:
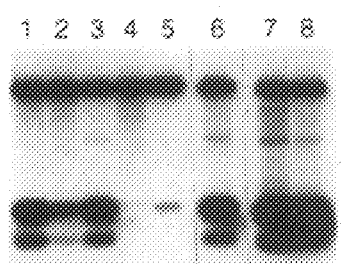
Figure 1D:
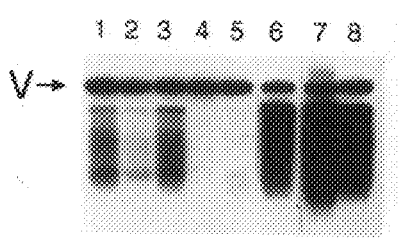
Figure 1E:
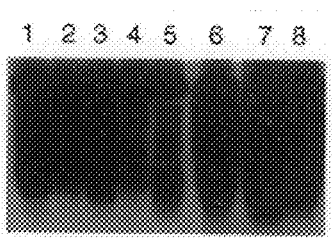
Figure 1F:
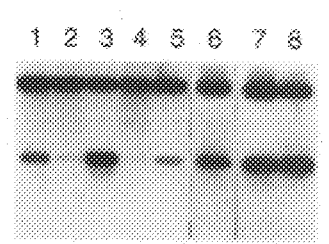
Figure 2:
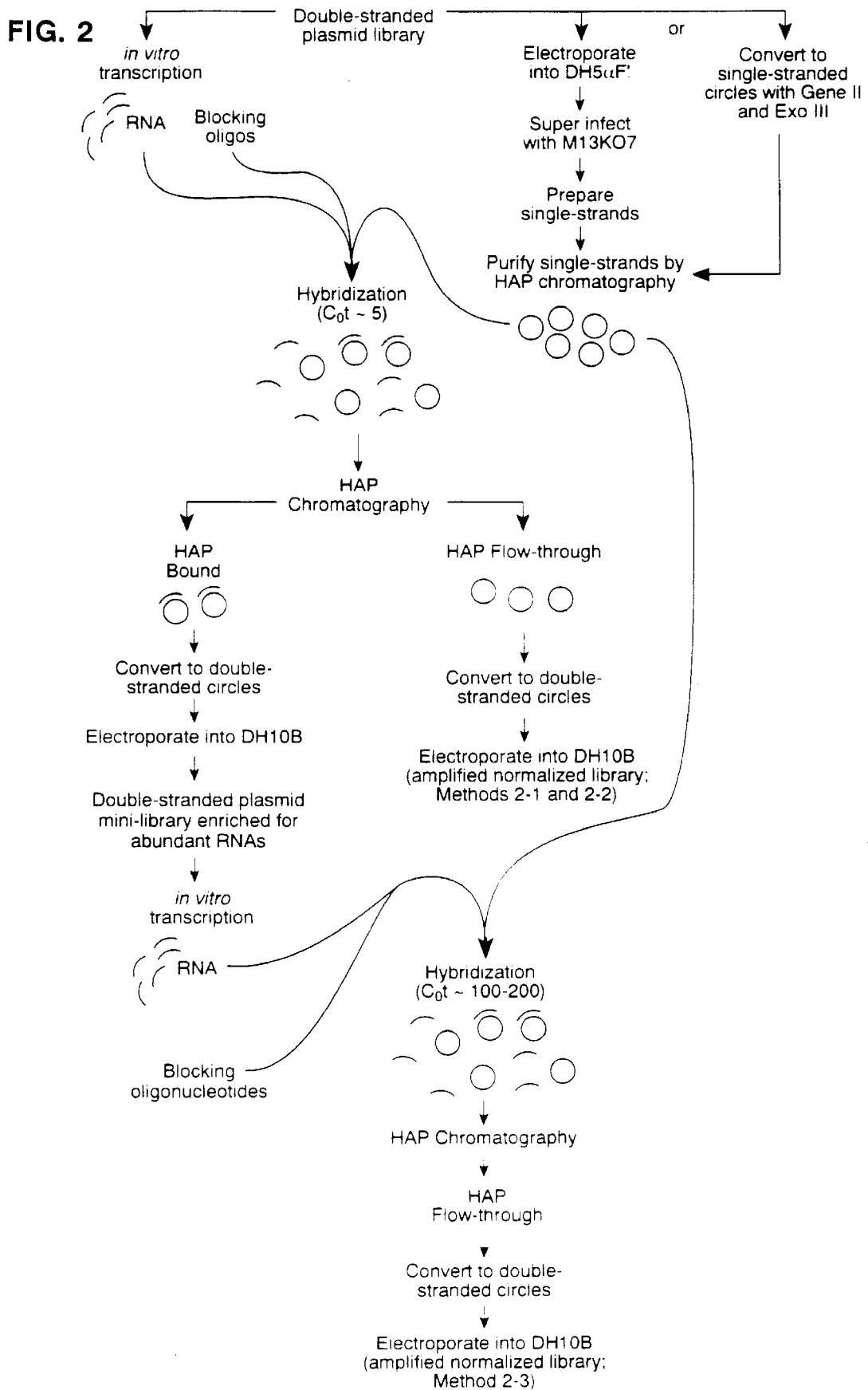
FIG. 2 Diagram of the normalization methods 2-1, 2-2 and 2-3

Reasoning that such a problem could be circumvented if
the fragments used in the hybridization with the single-
stranded circles (i) were in excess, and (ii) spanned the entire
length of the cDNAs, an alternative procedure to normalize
cDNA libraries was developed based on hybridization of in
vitro synthesized RNA (driver) from an entire library with
the library itself in the form of single-stranded circles
(tracer) (see Methods 2-1 and 2-2 in FIG. 2). Several
normalized libraries were generated by this procedure (see
Table 1).

Southern hybridization of endonuclease restricted plas-
mid DNA from starting and normalized libraries with a
number of cDNA probes (FIG. 1) clearly indicated that these
methods effectively improved the representation of full-
length cDNAs in the normalized libraries (e.g., compare
lanes 1 and 4 in panels A, D–E and G–H). However,
characterization of one of these libraries ($^5$Nb$^2$HFLS20W)
by colony hybridization with cDNA probes (Table 2) indi-
cated that this approach was effective to reduce the fre-
quency of some, but not all, of the most abundant clones
(e.g., serum albumin was reduced about 20 fold, whereas
γ-globin was only reduced two fold).

No difference was observed when hybridizations were
performed at different conditions (0.4M NaCl-50% forma-
mide at 42° C. as in methods 2-1 and 2-3; 0.12M NaCl-50%
formamide-1% SDS at 30° C. as in method 2-2, see lane 3
in FIG. 1; 0.4M NaCl-80% formamide at 42° C., not shown).

It is noteworthy that Northern hybridization (not shown)
of in vitro transcribed RNA synthesized from an entire
plasmid library with probes derived from the abundant
cDNAs that failed to be effectively normalized by this
procedure (e.g., globins in the fetal liver-spleen library and
G3PD in the breast library) indicated that they were not as
prevalent in the population of in vitro transcribed RNAs as
they were in their respective starting cDNA libraries.

A significantly improved extent of normalization was
achieved when run-off RNA synthesized from the plasmid
mini-library enriched for abundant cDNAs (HAP-bound
fraction of Method 2-1 in FIG. 2; see also Table 3) was
hybridized ($C_0t$=100–200) with single-stranded circles from
the starting library (see Method 2-3 in FIG. 2 and Table 1;
compare lanes 1 and 2 in panels A, B, C, D, F and G in FIG.
1).

In an effort to preserve the positive characteristics of both
methods 1 and 2 (i.e. the adequate extent of normalization
achieved with method 1, and the improved representation of full-length cDNAs achieved with method 2) two additional reassociation kinetics based procedures were developed involving DNA-DNA hybridization (methods 3 and 4; see FIG. 3).

Method 3, which was successfully used to construct a normalized library from multiple sclerosis plaques (see $^2$NbHMSP in Table 1), involved hybridization of a 20 fold excess of single-stranded cDNA fragments (comprising the 5' halves of all inserts of the starting library, generated by Exonuclease III digestion of gel purified double-stranded cDNAs; see FIG. 3) with complementary single-stranded circles produced in vitro by the combined action of Gene II and Exonuclease III (Life Technologies).

Southern hybridization of Not I+Eco RI digested plasmid DNA from starting and normalized (with methods 2-1 and 3) multiple sclerosis plaques library with mitochondrial 16S rRNA and myelin basic protein cDNA probes (not shown), clearly indicated that method 3 was superior to method 2-1 in that a much greater extent of normalization was achieved, at the same time that it maintained (similarly to method 2-1) appropriate representation of both full-length cDNAs.

For the libraries constructed with Method 4 (see Table 1 and FIG. 3), double-stranded cDNA inserts generated by PCR with T3 and T7 primers were melted and hybridized (in the presence of vast excess of blocking oligonucleotides) with single-stranded plasmid library DNA prepared in vitro.

Southern hybridization of Pac I+Eco RI digested plasmid DNA from starting and normalized (with methods 1, 2-1, 2-2, 2-3 and 4) fetal liver-spleen libraries (FIG. 1) with several cDNA probes (including those that revealed incomplete normalization with methods 2-1, 2-2 and 2-3, such as α-globin, β-globin and γ-globin) demonstrated the efficacy of method 4 to achieve the desired extent of normalization obtained with method 1 (compare lanes 1, 2, 3, 4, 5 and 6 in panels A, B, C, D, F, G–H, and lanes 3, 4, 5 and 6 in panels I, J and K in FIG. 1), while preserving the representation of full-length cDNAs (e.g., full-length albumin was present in the normalized library prepared with method 4, shown in lane 5 of panels D–E, but it was undetectable in the normalized library constructed with method 1, shown in lane 4; a similarly remarkable difference was revealed with the cDNA probe for H19 RNA, shown in panels G and H).

In order to assess further the ability of these normalization procedures to preferentially reduce the representation of the most abundant cDNAs, a comparative sequence analysis of 100 clones randomly picked from the fetal liver-spleen cDNA library normalized with Method 4 ($^{14}$Nb$^2$HFLS20W in Table 1; HAP-flow-through fraction in FIG. 3), and from two fetal liver-spleen mini-libraries enriched for abundant cDNAs (HAP-bound fractions in FIG. 2 and 3) obtained during HAP purification of the normalized libraries prepared according to methods 2–1 ($^5$Nb$^2$HFLS20W) and 4 ($^{14}$Nb$^2$HFLS20W) was performed. The results are summarized in Table 3. A number of cDNAs known to be prevalent in the starting fetal liver-spleen library (e.g., albumin, globins, mitochondrial RNAs, apolipoproteins) were found at increased frequencies in both mini-libraries enriched for abundant cDNAs, but none of them was represented in the sample of 100 clones from the normalized library. It is noteworthy that while 47% of the sequences derived from the normalized library were not represented in the "all non-redundant" subdivision of sequences of Genbank+ EMBL+DDBJ+PDB, the majority of the sequences obtained from the mini-libraries of abundant cDNAs derived from methods 2-1 and 4 (91.4% and 86.9%, respectively) did have homologous sequences in that database. Furthermore, although 49% of the sequences derived from the normalized library had fewer than 10 homologous ESTs in the dbEST subdivision of Genbank, most of the sequences obtained from both mini-libraries had greater than 10 homologous ESTs in the dbEST database (92.5% and 89.7%, respectively, in the HAP-bound fractions of methods 2-1 and 4).

With the ultimate goal of facilitating the ongoing process of gene discovery by large scale sequencing of cDNA clones randomly picked from libraries, a pilot subtractive hybridization experiment was performed to eliminate (or reduce representation of) a pool of approximately 5,000 I.M.A.G.E. Consortium arrayed cDNA clones (pool # 1, LLAM 78–90) from the normalized library from which they were derived ($^1$NFLS in Table 1). PCR-amplified cDNA inserts from pool # 1 were melted and hybridized, in the presence of blocking oligonucleotides, with single-stranded plasmid DNA from the $^1$NFLS library, prepared in vitro. The remaining single-stranded circles were purified by HAP chromatography, converted to double-stranded plasmids, electroporated into bacteria and propagated under antibiotic selection to generate the subtractive $^1$NFLS-S1 library. Preliminary characterization of the $^1$NFLS-S1 library by Southern hybridization with ten cDNA probes (only five are shown; see FIG. 5) known to be represented in pool # 1, clearly indicated the effectiveness of the procedure to eliminate (or to reduce the representation of) all eleven cDNA sequences from (in) the $^1$NFLS library. A BLASTN search of the dbEST division of Genbank (6/12/96) with 3' ESTs obtained from the five probes (cDNAs -1, -4, -8, -9 and -10) whose hybridizations were not shown in FIG. 5, revealed the presence of 0, 0, 1, 2 and 2 corresponding ESTs, respectively, from the $^1$NFLS library, thus indicating that the subtraction was successful even for cDNAs that were underrepresented in the normalized library (a total of 44,407 3' ESTs have been derived from the $^1$NFLS library to date). It should be noted that due to sequencing failures, some of the clones in these arrays may not yet have corresponding ESTs in the public databases.

It is noteworthy that when the same subtractive hybridization experiment was attempted to be performed using as driver, RNA synthesized in vitro from a plasmid DNA preparation of pool # 1, the results obtained were not satisfactory (not shown) in that subtraction could be demonstrated for some but not all tested clones (e.g, α-globin could not be effectively subtractive), similarly to what was observed in normalizations with method 2-1.

Experimental Discussion

As a result of an effort to improve the representation of full-length cDNAs in normalized libraries, four different methods for normalization of directionally cloned cDNA libraries constructed in phagemid vectors were developed, while contributing resources to the I.M.A.G.E. Consortium (Lennon et al., 1996) and thereby facilitating the ongoing gene discovery and mapping programs. Approximately 87.5% of all (human) I.M.A.G.E. ESTs were derived from the normalized libraries described here.

The normalization procedure (method 1) that was described previously (Soares et al. 1994) was applied for the construction of the $^1$NIB and $^1$NFLS normalized libraries, from which a total of 45,192 and 86,088 ESTs, respectively, have been derived (dbEST release 052396; http://www.ncbi.nlm.nih.gov). Data analysis (Hillier et al. 1996, in press) solidly demonstrated the efficacy of this approach to bring the frequency of all clones to within a narrow range.

Extensive characterization of these two libraries by Southern analysis, however, revealed that on occasion truncated clones were favored over their full-length counterparts during the normalization procedure.

Due to the relatively permissive conditions used for synthesis of first-strand cDNA, priming with the Not I-tag-[dT]$_{18}$ oligonucleotide may occur not only at the poly(A) tail of the mRNAs but also at internal A-rich sites within the mRNAs (e.g., at Alu tails). Typically, cDNAs with 3' truncations occur at frequencies of 10–15% in directionally cloned libraries (Berry et al. 1995). Truncated clones can be (tentatively) recognized as such, by the absence of a bona fide polyadenylation signal sequence at the appropriate distance upstream from the oligo-[dA]$_{18}$ tail of the cDNA.

Truncated cDNAs may be favored over their full-length counterparts during normalization by Method 1. Briefly, Method 1 (Soares et al. 1994) involves: (i) annealing of a single-stranded DNA preparation of a directionally cloned cDNA library with an oligo [dT]$_{18}$ primer, (ii) controlled primer extension reactions in the presence of deoxynucleotides and dideoxynucleotides to generate 3' noncoding extension products of approximately 200–300 nucleotides, (iii) purification of the resulting partially double-stranded circles by HAP chromatography, (iv) melting and reassociation of the HAP-purified partially double-stranded circles to a relatively low $C_0t$ (5–10), (v) purification of the remaining single-stranded circles (normalized library) over HAP, (vi) conversion of the single-stranded circles to double-stranded circles, and (vii) electroporation into bacteria.

It could be anticipated that during the reassociation reaction, since truncated cDNAs occur at lower frequencies than their non truncated counterparts, the extension products of the truncated cDNAs would more likely reanneal to the non truncated overlapping cDNAs than to their own truncated templates. On the other hand, the extension products of the non truncated cDNAs would most likely reassociate to their own non truncated templates not only because they are more prevalent but also because of the low probability of there being an overlap between the short extension product of a non truncated clone and a truncated single-stranded circle. As a result, non truncated single-stranded circles are more likely to end up reassociated with more than one (non overlapping) extension products, whereas their truncated counterparts would remain single-stranded and therefore end up in the HAP-flow-through fraction (normalized library).

Reasoning that this problem could be circumvented (i) if the hybridizing fragments were in excess over single-stranded circles, and (ii) spanned the entire length of the cDNAs to maximize the opportunity of overlap between truncated and non truncated clones, an approach was devised(methods 2-1 and 2-2; note that 2-2 is the same as 2-1 except that hybridization conditions were different) whereby in vitro synthesized RNA from a plasmid DNA preparation of a starting library is used as driver in hybridization ($C_0t$~5) with the same library in the form of single-stranded circles. Indeed, these modifications successfully improved the representation of full-length cDNAs in the normalized libraries (e.g., serum albumin in the liver-spleen libraries).

However, in every library constructed with methods 2-1 and 2-2, cDNA clones that seemed to become normalized with much greater difficulty than others were able to be identified (e.g., α-globin in the $^5$Nb$^2$HFLS20W liver-spleen library, and G3PD in the breast library). These results were interpreted as suggestive that not all clones might be transcribed in vitro with the same efficiency if in a mixture (i.e., in vitro transcription of plasmid DNA from an entire library) and/or secondary structures in the RNAs (or interactions between RNAs) might impair their ability to hybridize with the single-stranded circles. These hypotheses were corroborated by the observation (not shown) that relatively weak hybridization signals were observed when Northern blots of RNA transcribed in vitro from an entire plasmid library were hybridized with cDNA probes derived from those clones that could not be normalized as effectively, despite the fact that they occurred at high frequencies in the starting libraries from which the in vitro transcribed RNAs were synthesized. The possibility that the clones that were not being effectively normalized carried deletions that prevented them from being appropriately transcribed in vitro was excluded (not shown). In fact, all clones that were tested individually for in vitro transcription yielded the expected amounts of full-length RNA. Although this problem was significantly minimized in method 2-3 (compare lanes 1 and 2 in panels A, B, C, D, F and G in FIG. 1), the extent of normalization that was achieved was still not comparable to that obtained with method 1 (compare lanes 2 and 4 in panels A, B, C, D, F and H in FIG. 1).

The advantage of method 2-3 over methods 2-1 and 2-2 is that the RNA driver is derived from a mini-library (of relatively low complexity) enriched for abundant cDNAs rather than from the entire starting library. For this reason, higher $C_0t$ hybridizations can be carried out to eliminate or significantly reduce the representation of the most abundant cDNAs. It should be noted, however, that method 2-3 is not a true normalization procedure since what is aimed to be accomplished with this approach is not to equalize the frequency of all cDNA clones but rather to reduce significantly (or even to eliminate, depending on the $C_0t$ used) the representation of the most abundant clones.

The extent to which the enrichment for abundant transcripts can be achieved in such mini-libraries depends essentially on the $C_0t$ used for reassociation. Calculations based on estimates of frequencies of brain mRNAs (Soares et al. 1994) indicate that the best enrichments are obtained at a $C_0t$=5–10. If the $C_0t$ is too low ($\leq 1$) the enrichment is only for the most prevalent (class I) mRNAs; there is no enrichment for the mRNAs of the intermediate frequency class (class II) mRNAs. On the other hand, if the $C_0t$ is too high ($\geq 50$) the enrichment for class I transcripts starts to become less significant due to a higher representation of mRNAs of the complex class (class III). Prevalent and intermediate (classes I+II) brain mRNAs comprise 93–95% of the total cDNA population in a $C_0t$=5–10 HAP-bound mini-library, in contrast to 62% in the starting library. Consequently, the frequency of class III transcripts in a $C_0t$=5–10 HAP-bound mini-library is about 5.5 fold lower than that of the starting library (5–7% in the bound mini-library versus 38% in the starting library).

Methods 3 and 4 were developed as a result of an attempt to achieve both the adequate extent of normalization obtained with method 1 and the improved representation of full-length cDNAs accomplished with methods 2-1, 2-2 and 2-3. Although more technically cumbersome, Method 3 is advantageous over method 4 in that the DNA driver used in the hybridization is single-stranded.

Single-stranded driver in Method 3 (see FIG. 3) is generated by Exonuclease III digestion of gel purified double-stranded cDNA inserts excised from the starting library. The resulting non complementary single-stranded fragments represent the 5' and 3' halves of the original cDNA inserts. The fragments that correspond to the 5' halves of the cDNAs are complementary to single-stranded circles prepared in vitro, whereas the single-stranded fragments that correspond to the 3' halves of the cDNA inserts are complementary to single-stranded plasmids prepared in vivo. Note that for the multiple sclerosis plaques library constructed with Method 3 single-stranded circles prepared in vitro were used.

Production of single-stranded circles in vitro by the combined action of Gene II and Exonuclease III (Life Technologies), rather than in vivo by superinfection of a culture with a helper phage, is very advantageous because it circumvents the distortions that otherwise may arise as a result of the differential growth properties of clones with different size inserts. However, since the digestion with Gene II results in the conversion of most, but not all, supercoiled plasmids to relaxed circles, it becomes necessary to purify the single-stranded circles that are produced after digestion with Exonuclease III by HAP chromatography.

For construction of the normalized multiple sclerosis plaques library, the cDNA inserts were excised by double digestion of plasmid DNA from the starting library with Not I and Eco RI. The fact that one in every three clones might have an internal Eco RI site (an Eco RI site is expected to occur once every 4,096 bp, and the average insert size in these libraries is of the order of 1.4 kb) should not compromise the efficiency of the procedure because at least one of the resulting restriction fragments would be expected to be $\geq 200$ bp (clones smaller than 400 bp are size selected out of these libraries) and therefore be able to form hybrids that would bind quantitatively to HAP under these conditions. A disadvantage of method 3, as presented, is that only clones <2.9 kb (approximate vector size) can be cleanly excised from the vector. It is conceivable, however, that one might be able to use double-stranded cDNA fragments generated by PCR amplification with T3 and T7 primers as substrate for the Exonuclease III digestion in method 3.

Method 4 was used to generate a significant fraction of the libraries that were contributed to the I.M.A.G.E. Consortium (see Table 1). It is undoubtedly the simplest and overall most advantageous of all procedures. Because the DNA driver is generated by PCR amplification of the starting (double-stranded or single-stranded, see below) plasmid library with T3 and T7 primers, the tracer (single-stranded circles) used in this hybridization may be produced in vitro or in vivo.

The extent of normalization achieved with Method 4 was comparable to that obtained with method 1 with the advantage that it successfully preserved the representation of full-length cDNAs (compare lanes 4 and 5 in FIG. 1). Moreover, method 4 is advantageous over Method 1 because it does not preclude the clones derived from mRNAs with internal Not I sites from being represented in the normalized library. Since the starting material for the reassociation kinetics reaction in Method 1 is generated by a controlled primer extension reaction with an oligo-[dT]$_{18}$ primer, clones without an oligo-[dA]$_{18}$ tail (derived from mRNAs with an internal Not I site) are not represented in the final normalized library, although they are not necessarily lost (clones without tail end up in the HAP flow-through fraction during HAP purification of the partially double-stranded circles generated by this primer extension reaction). It should also be noted that this problem of Method 1 could be circumvented by the use of an oligonucleotide complementary to flanking vector sequences (as opposed to the oligo-[dT]$_{18}$) for this controlled primer extension reaction.

The potential biases introduced by PCR amplification in method 4 are minimized by the fact that (i) PCR amplification products are used in excess in these hybridizations, and (ii) the size distribution of inserts in these libraries is relatively narrow (typically ranging from 0.4–2.5 kb).

The conditions used for hybridization greatly influenced the quality of the resulting normalized libraries constructed with method 4. This is to a great extent a consequence of the fact that HAP is used to purify single-stranded circles, as opposed to a biotin-avidin capture system, which yielded significantly less satisfactory results (Bonaldo and Soares, unpublished results). The best results were obtained when the hybridization conditions were the most similar to the HAP conditions. For example, globin cDNAs in the fetal liver-spleen library were normalized much more effectively when the hybridization was performed at 30° C. in 0.12M NaCl-50% formamide-10 mM Tris pH8.0-5 mM EDTA-1% SDS than at 42° C. in 0.4M NaCl-50% formamide-10 mM Tris pH8.0-5mM EDTA-or even at 42° C. in 0.12M NaCl-50% formamide-10 mM Tris pH8.0-5mM EDTA without SDS. These results were interpreted as suggestive of the fact that imperfect hybrids formed during hybridization may either not bind to HAP and/or may melt once in the HAP buffer.

It is noteworthy that a much superior extent of normalization was obtained with method 4 when single-stranded plasmid DNA prepared in vitro, as opposed to double-stranded plasmid DNA, was used as template for PCR amplification (not shown). These results were interpreted as indicative that a fraction of the double-stranded plasmids used as template for PCR amplification, presumably in the form of melted supercoiled DNA, might end up in the HAP-flow-through fraction (normalized library) during purification.

It is noteworthy that cross-hybridizing diverged sequences seem to escape normalization, in all of the procedures discussed above. For example, the frequency of Alu repeat-containing cDNAs (typically 10% in directionally cloned cDNA libraries) is practically the same in starting and normalized libraries. These results were interpreted as suggestive that imperfect hybrids either do not bind to HAP under these conditions, or melt once diluted in the (more stringent) HAP buffer. This is advantageous, not only because it preserves the representation of Alu-containing cDNAs that might correspond to otherwise rare mRNAs, but also, and most significantly, because it minimizes the likelihood that a rare member of a gene family might be excluded from the final (normalized or subtractive) library as a result of a cross-hybridization with a more prevalent but diverged sequence.

The use of normalized libraries for large scale gene discovery/EST programs is advantageous because it minimizes redundancies while increasing the representation of the rarer cDNAs by about 3 fold, in average. However, given the great extent of overlap in gene expression among different tissues, the use of normalized libraries alone is not sufficient to maintain a desirable pace of identification of novel sequences at advanced stages of such programs. For this reason, it is proposed that the use of subtractive libraries enriched for clones not yet identified might become increasingly advantageous. In an effort towards this goal,a subtractive hybridization approach designed specifically for this purpose was developed (see FIG. 4). In a pilot experiment, the representation of approximately 5,000 [1]NFLS-I.M.A.G.E. Consortium clones from the NFLS library itself was significantly reduced (see FIG. 5). With the development of appropriate clustering algorithms, the use of non-redundant sets of cDNA/gene sequences as drivers for hybridizations to generate subtractive libraries enriched for novel sequences should soon become possible, and thus hopefully facilitate the isolation of all human and mouse cDNAs still awaiting identification.

TABLE 1

Complete list and main features of the normalized human, mouse, rat and Schistosome cDNA libraries.

| mRNA Source | Normalized Library Name | Number of Recombinants in the Normalized Library | Preparation of Single-Stranded Plasmids | Method of Normalization | Library Tag |
|---|---|---|---|---|---|
| human infant brain | [1]NIB | 2,500,000 | in vivo | 1 | AGGAA |
| human fetal liver-spleen | Nb[2]HFLS20W (1NFLS) | 19,000,000 | in vivo | 1 | AGATCT |
|  | [5]Nb[2]HFLS20W | 3,200,000 | in vitro | 2-1 |  |
|  | [6]Nb[2]HFLS20W | 1,400,000 | in vitro | 2-3 |  |
|  | [14]Nb[2]HFLS20W | 3,200,000 | in vitro | 4 |  |
|  | [15]Nb[2]HFLS20W | 35,000,000 | in vitro | 2-2 |  |
| human term placenta | Nb[2]HP | 750,000 | in vivo | 2-1 | AGGA |
| human 8-9W placenta | [2]NbHP8-9W | 100,000 | in vitro | 2-3 | GA |
| human breast | [2]NbHbst-[3]NbHBst | 2,090,000 | in vivo | 2-1 | CC |
| human adult brain | N[2]b[4]HB55Y-N[2]b[5]HB55Y | 3,170,000 | in vivo | 2-1 | GC |
| human retina | [2]N[2]b[4]HR-N[2]b[5]HR | 1,600,000 | in vivo | 2-1 | AC |
| human pineal gland | [3]NbHPG | 1,000,000 | in vitro | 2-1 | CG |
| human ovary tumor | NbHOT | 1,100,000 | in vivo | 2-1 | GG |
| human melanocytes | [2]NbHm | 6,800,000 | in vitro | 2-3 | AG |
| human fetal heart | NbHH19W | 9,700,000 | in vitro | 4 | ATC |
| human parathyroid adenoma | NbHPA | 3,400,000 | in vitro | 4 | ACCAA |
| human senescent fibroblast | NbHSF | 9,900,000 | in vitro | 4 | AACCA |
| human multiple sclerosis plaques | [2]NbHMSP | 1,100,000 | in vitro | 3 | CA |
| human fetal lung | NbHL19W | 21,700,000 | in vitro | 4 | AA |
| 19.5 dpc mouse embryo | p[3]NMF 19.5 | 3,400,000 | in vitro | 4 | ACAAC |
| 17.5 dpc mouse embryo | NbME 17.5 | 6,800,000 | in vitro | 4 | GACAC |
| 13.5–14.5 dpc mouse embryos | NbME 13.5–14.5 | 380,000 | in vitro | 4 | GGAAA |
| rat heart | NbRH | 400,000 | in vitro | 4 | ACAAC |
| rat kidney | [2]NbRK | 130,000 | in vitro | 4 | CAAAC |
| 8 week adult Schistosome | NbS8W | 1,000,000 | in vitro | 4 | GAAAG |

Table 1 legend:
Complete list and main features of the normalized human, mouse, rat and Schistosome cDNA libraries. The human fetal liver-spleen cDNA library ([2]HFLS20W) was normalized by methods 1, 2-1, 2-2, 2-3 and 4. With the exception of [1]NIB which was constructed in the Lafmid BA vector, all other libraries were constructed in the pT7T3-Pac vector. Cloning sites were Not I and Eco RI, except for fetal liver-spleen (Pac I and Eco RI) and infant brain (Not I and Hind III). The library tag is a sequence identifier present in the oligonucleotide used to prime the synthesis of first-strand cDNA, between the recognition sequence for the rare restriction enzyme (Not I, or Pac I in the case of the liver-spleen library) used for directional cloning and the $dT_{18}$ stretch (or $dT_{25}$ in the human parathyroid adenoma, senescent fibroblast, mouse embryo, rat and Schistosoma mansoni libraries) located at the 3' end of the primer. [2]NbHbst differs from [3]NbHbst in the $C_0t$ used for hybridization (237 and 20, respectively). $N^2b^4HB55Y$ and $^2N^2b^4HR$ differ from $N^2b^5HBSSY$ and $N^2b^5HR$, respectively, in the average size of their cDNA inserts (1.5–2.5 kb and 0.4–1.5 kb, respectively). Human infant brain (kindly provided by Dr. Conrad Gilliam, Columbia University) was from a 72 day old female who died in consequence of spinal muscular atrophy; human fetal liver-spleen (kindly provided by Dr. Stephen Brown, Columbia Presbyterian Medical Center) was from a 20 week post conception normal female; total cellular poly(A) + mRNA from normal breast pooled from reduction mammoplasty tissue was kindly provided by Dr. Anne Bowcock and Ms. Monique Spillman, The University of Texas Southwestern Medical Center at Dallas; total cellular adult brain RNA (kindly provided by Dr. Donald Gilden, University of Colorado Health Sciences Center) was obtained from a 55-year old male who died of a ruptured aortic aneurysm. Brain tissue (frontal, parietal, temporal and occipital cortex from the left and right hemispheres, subcortical white matter, basal ganglia, thalamus, cerebellum, midbrain, pons and medulla) was acquired 17-18 hours after death; total cellular normal human retina RNA (kindly provided by Dr. Roderick R. McInnes, University of Toronto and Hospital for Sick Children, Canada) was obtained from a 55 year old Caucasian male; human pineal gland (kindly provided by Dr. David Klein, National Institute of Child Health and Human Development) was derived from a group of three pineal glands (gland 1: 48 year-old Caucasian male; gland 2: 18 year-old Caucasian female, gland 3: 20 year-old African American male); total cellular human ovary tumor mRNA was kindly provided by Dr. Anne Bowcock, The University of Texas Southwestern Medical School and it was obtained from a 36 year old Caucasian with a papillary serous cystadenocarcinoma grade III with surface extensions and metastases; total

TABLE 1-continued

Complete list and main features of the normalized human, mouse, rat and Schistosome cDNA libraries.

| mRNA Source | Normalized Library Name | Number of Recombinants in the Normalized Library | Preparation of Single-Stranded Plasmids | Method of Normalization | Library Tag |
|---|---|---|---|---|---| cellular human melanocyte RNA (kindly provided by Dr. Anthony Albino and Dr. Alice de Oliveira, Memorial Sloan-Kettering Cancer Center) was derived from normal foreskin; normal human fetal heart and lung (kindly provided by Dr. Stephen Brown, Columbia Presbyterian Medical Center) were derived from the same 19 week post conception specimen; human parathyroid tumor (kindly provided by Dr. Stephen Marx, National Institute of Diabetes and Digestive and Kidney Diseases, NIH) was derived from sporadic adenomas; cytoplasmic mRNA from senescent normal human fibroblasts was kindly provided by Dr. Barbara Burkhart (National Institute of Environmental Health Sciences, NIH). The cells were prepared by passaging normal human fibroblasts derived from foreskin until they exhibited an enlarged, flattened phenotype and failure to divide (labeling index of <2% following 48 h BrdU incorporation); total cellular RNA from multiple sclerosis plaques (kindly provided by Dr. Kevin G. Becker, NINDS, NIH) was extracted from four lesions obtained from one patient. Total cellular RNA for construction of the mouse (C57BL/6J strain) embryonic libraries was kindly provided by Dr. Minoru Ko (Wayne State University). Rat tissues were obtained from an adult Zivic-Miller Sprague Dawley female and were kindly provided by Dr. Stephen Brown (Columbia Presbyterian Medical Center). Total cellular RNA from mature 8 week old Schistosoma mansoni worms was kindly provided by Dr. Ron Blanton, Case Western Reserve University.

TABLE 2

Comparison of the frequencies of cDNA probes in the starting and three normalized fetal liver-spleen cDNA libraries.

| cDNA Probe | Starting Library | Normalized Method 1 | Normalized Method 2-1 | Normalized Method 4 |
|---|---|---|---|---|
| γ-Globin | 9.2% (46/500) | ND | 4.3% (130/3000) | 0.04% (5/14,000) |
| Serum Albumin | 8.6% (43/500) | 0.3% (2/598) | 0.4% (4/1,121) | 0.42% (59/14,000) |
| α-Globin | 6.4% (32/500) | ND | ND | 0.02% (3/14,000) |
| β-Globin | 3.6% (18/500) | ND | ND | 0.01% (1/14,000) |
| H19 RNA | 1.8% (88/5000) | ND | ND | 0.11% (16/14,000) |
| Apolipoprotein A | 1.18%.(59/5000) | ND | 0.2% (2/1,121) | 0.02% (3/14,000) |
| Ferritin | 1% (2/202) | 0.2% (1.598) | 0.3% (3/1,121) | ND |
| Mitochondrial Cytochrome Oxidase | 0.48% (24/5000) | ND | ND | 0.07% (10/14,000) |
| Aldolase | 0.4% (22/5000) | ND | 0.03% (13/50,000) | ND |
| Acidic Ribosomal phosphoprotein | 0.26% (13/5000) | ND | ND | 0.03% (4/14,000) |
| Apolipoprotein H | 0.14% (7/5000) | ND | ND | 0.14% (20/14,000) |
| Angiotensinogen | 0.12% (6/5000) | ND | 0.1% (46/50,000) | 0.13% (18/14,000) |
| Translationally Controlled Tumor Protein | 0.1% (42/60,000) | ND | 0.02% (8/50,000) | ND |
| Ribosomal Protein S20 | 0.1 (4/5000) | ND | 0.01% (3/50,000) | ND |
| Transferrin | <0.02% (0/5000) | ND | ND | 0.06% (8/14,000) |
| Mouse sterility complex | 0.015% (15/100,000) | ND | 0.01% (4/50,000) | ND |
| Unknown cDNA 3 | 0.01% (4/60,000) | 0.02% (14/60,000) | 0.01% (7/100,000) | ND |

Table 2 legend
Comparison of the frequencies of CDNA probes in the starting and three normalized fetal liver-spleen cDNA libraries. The indicated percentages of the cDNA probes in the starting (b$^2$HFLS20W) and three normalized (method 1: $^1$NFLS; method 2-1: $^5$Nb$^2$HFLS20W; method 4: $^{14}$Nb$^2$HFLS20W) liver-spleen cDNA libraries are shown in order of decreasing frequency in the b$^2$HFLS20W library. Frequencies were calculated from the number of positive colonies after hybridization of duplicate filters containing 500–100,000 colonies from each of the four cDNA libraries. Colony hybridization experiments were performed as previously described (Soares et al., 1994). Unknown cDNA was randomly picked from a fetal liver-spleen subtractive library. ND, non determined.

TABLE 3

Comparative sequence analysis of about 100 fetal liver-spleen clones randomly picked from each of two mini-libraries enriched for abundant cDNAs and the normalized library constructed with method 4.

| cDNA Sequences | Normalized Method 4 | HAP-Bound Method 4 | HAP-Bound Method 2-1 |
| --- | --- | --- | --- |
| Serum Albumin | 0/100 | 15/107 | 18/93 |
| γ-Globin | 0/100 | 10/107 | 5/93 |
| α-Globin | 0/100 | 4/107 | 4/93 |
| Mitochondrial Genome | 0/100 | 4/107 | 16/93 |
| β-Globin | 0/100 | 2/107 | 4/93 |
| Apolipoprotein A | 0/100 | 2/107 | 1/93 |
| Apolipoprotein H | 0/100 | 2/107 | 1/93 |
| Calpastatin | 0/100 | 2/107 | 0/93 |
| Transferrin | 0/100 | 2/107 | 0/93 |
| α 1-Antitrypsin | 0/100 | 2/107 | 0/93 |
| Angiotensinogen | 1/100 | 2/107 | 1/93 |
| Placental lactogen | 0/100 | 1/107 | 5/93 |
| Insulin-like growth factor II | 0/100 | 0/107 | 2/93 |
| Serum Vitamin D | 0/100 | 0/107 | 2/93 |
| Not Represented in the NR Database | 47% (47/100) | 13.1% (14/107) | 8.6% (8/93) |
| Not Represented in either the NR or the dbEST Database | 15% (15/100) | 2.8% (3/107) | 2.15% (2/93) |
| With <10 Similar ESTs in the dbEST Database | 49% (49/100) | 10.3% (11/107) | 7.5% (7/93) |
| With ≦2 ESTs in the dbEST Database | 29% (29/100) | 5.6% (6/107) | 4.3% (4/93) |

Table 3 legend
Comparative sequence analysis of about 100 fetal liver-spleen clones randomly picked from each of two mini-libraries enriched for abundant CDNAs and the normalized library constructed with method 4. A total of 100 clones from the normalized (HAP Flow-Through) fetal liver-spleen library constructed with method 4 ($^{14}$Nb$^{2HFLS20W}$), 107 clones from the HAP-Bound fraction obtained during HAP purification of the $^{14}$Nb$^{2}$HFLS20W library (see Table 1 and FIG. 3), and 93 clones from the HAP Bound fraction obtained during HAP purification of the $^{5}$Nb$^{2}$HFLS20W library constructed with method 2-1 (see Table 1 and FIG. 2) were randomly picked and sequenced from the 3' end. HAP-bound fractions were here designated as "mini-libraries enriched for abundant cDNAs". Double-stranded plasmid DNA templates were prepared using the Wizard Minipreps DNA purification system (Promega) and cycle sequenced using the universal forward fluorescent primer Perkin Elmer). Reaction products were analyzed on an automated 370A DNA sequencer (Applied Biosystems). Nucleic acid and protein database searches were performed at the National Center for Biotechnology Information server using the BLAST algorithm (Altschul et al., 1990). NR = All Non-redundant GenBank + EMBL + DDBJ + PDB sequences (but no EST's or STS's); dbEST = Non-redundant Database of GenBank + EMBL + DDBJ EST Divisions.

References
1. Adams, M. D., J. M. Kelley, J. D. Gocayne, M. Dubnick, M. H. Polymeropoulos, H. Xiao, C. R. Merril, A. Wu, B. Olde, R. F. Moreno, A. R. Kerlavage, W. R. McCombie and J. Craig Venter. 1991. Complementary DNA Sequencing: expressed sequence tags and Human Genome Project. Science 252: 1651–1656.
2. Adams, M. D., M. Dubnick, A. R. Kerlavage, R. Moreno, J. M. Kelley, T. R. Utterback, J. W. Nagle, C. Fields and J. Craig Venter. 1992. Sequence identification of 2,375 human brain genes. Nature 355: 632–634.
3. Adams, M. D., A. R. Kerlavage, C. Fields and J. C. Venter. 1993a. 3,400 new expressed sequence tags identify diversity of transcripts in human brain. Nature Genetics 4: 256–67.
4. Adams, M. D., A. R. Kerlavage, R. D. Fleischmann, R. A. Fuldner, C. J. Bult et al. 1995. Initial assessment of human gene diversity and expression patterns based upon 83 million nucleotides of cDNA sequence. Nature 377: 3–174.
5. Adams, M. D., M. B. Soares, A. R. Kerlavage, C. Fields and J. C. Venter. 1993b. Rapid cDNA sequencing (expressed sequence tags) from a directionally cloned human infant brain cDNA library. Nature Genetics 4: 373–80.
6. Altschul, S. F., W. Gish, W. Miller, E. Myers and D. J. Lipman. 1990. Basic Local Alignment Search Tool. J. Mol. Biol. 215: 403–410.
7. Barnes, W. M. 1994. PCR amplification of up to 35-kb DNA with high fidelity and high yield from lambda bacteriophage templates. Proc. Natl. Acad. Sci. (USA) 91: 2216–20.
8. Berry, R., T. J. Stevens, N. A. Walter, A. S. Wilcox, T. Rubano, J. A. Hopkins, J. Weber, R. Goold, M. B. Soares, and J. M. Sikela. 1995. Gene-based sequence-tagged-sites (STSs) as the basis for a human gene map. Nature Genetics 10: 415–23.
9. Bishop, J. O., J. G. Morton, M. Rosbash and M. Richardson, 1974. Three abundance classes in HeLa cell messenger RNA. Nature 250: 199–204.
10. Davidson, E. H., and R. J. Britten. 1979. Regulation of gene expression: possible role of repetitive sequences. Science 204: 1052–9.
11. Hoheisel, J. D. 1993. On the activities of *Escherichia coli* exonuclease III. Analytical Biochemistry 209: 238–46.
12. Houlgatte, R., R. Mariage-Samson, S. Duprat, A. Tessier, S. Bentolila et al. 1995. The Genexpress Index: a resource for gene discovery and genic map of the human genome. Genome Research 5: 272–304.
13. Johnston, S., J. H. Lee and D. S. Ray. 1985. High-level expression of M13 gene II protein from an inducible polycistronic messenger RNA. Gene 34: 137–45.
14. Khan, A. S., A. S. Wilcox, M. H. Polymeropoulos, J. A. Hopkins, T. J. Stevens, M. Robinson, A. K. Orpana and J. M. Sikela. 1992. Single pass sequencing and physical and genetic mapping of human brain cDNAs. Nature Genetics 2: 180–5.
15. Lennon, G. G., C. Auffray, M. Polymeropoulos and M. B. Soares. 1996. The I.M.A.G.E. Consortium: An Integrated Molecular Analysis of Genomes and their Expression. Genomics 33: 151–152.

16. Matsubara, K., and K. Okubo. 1993. Identification of new genes by systematic analysis of cDNAs and database construction. Current Opinion in Biotechnology 4: 672–7.
17. McCombie, W. R., M. D. Adams, J. M. Kelley, M. G. FitzGerald, T. R. Utterback, M. Khan, M. Dubnick, A. R. Kerlavage, J. C. Venter and C. Fields. 1992. *Caenorhabditis elegans* expressed sequence tags identify gene families and potential disease gene homologues. Nature Genetics 1: 124–31.
18. Okubo, K., N. Hori, R. Matoba, T. Niiyama, A. Fukushima, Y. Kojima and K. Matsubara. 1992. Large scale cDNA sequencing for analysis of quantitative and qualitative aspects of gene expression. Nature Genetics 2: 173–9.
19. Rasched, I., and E. Oberer. 1986. Ff coliphages: structural and functional relationships. Microbiological Reviews 50: 401–27.
20. Scares, M. B. 1994. Construction of directionally cloned cDNA libraries in phagemid vectors. In *Automated DNA Sequencing and Analysis* (eds. M. D. Adams, C. Fields and J. Craig Venter), pp. 110–114. Academic Press, New York.
21. Soares, M. B., M. F. Bonaldo, P. Jelenc, L. Su, L. Lawton and A. Efstratiadis. 1994. Construction and characterization of a normalized cDNA library. Proc. Natl. Acad. Sci. (USA) 91: 9228–32.
22. Vieira, J., and J. Messing. 1987. Production of single-stranded plasmid DNA. Methods in Enzymology 153: 3–11.

---

What is claimed is:

1. A method to normalize a cDNA library comprising:
   (a) providing a cloned library containing cDNA inserts in circular double-stranded form wherein the inserts are capable of being amplified by polymerase chain reaction using appropriate primers;
   (b) converting the double-stranded cDNA library into single-stranded DNA circles;
   (c) generating single-stranded nucleic acid molecules complementary to the inserts of the single-stranded DNA circles converted in step (b) by polymerase chain reaction with appropriate primers and melting double-stranded cDNA inserts produced by the polymerase chain reaction;
   (d) hybridizing the single-stranded DNA circles converted in step (b) with the complementary single-stranded nucleic acid molecules generated in step (c) to produce partial duplexes at an appropriate Cot; and
   (e) separating unhybridized single-stranded DNA circles from hybridized DNA circles, thereby generating a normalized cDNA library.

2. A method of claim 1, wherein the cDNA library is constructed in the pT7T3-Pac vector.

3. A method of claim 1, wherein the cDNA library is a directional cDNA library.

4. A method of claim 1, wherein the cDNA library is a randomly-primed cDNA library.

5. A method of claim 3, wherein the directional cDNA library is generated by using a primer of oligodT stretch.

6. A method of claim 5, wherein the directional cDNA library is generated by using a primer having a rare restriction enzyme recognition site for the first strand cDNA synthesis, upstream of the oligodT stretch.

7. A method of claim 6, wherein the rare restriction enzyme recognition site is Not I or Pac I site.

8. A method of claim 6, wherein the primer contains a specific sequence between the sequence of the rare restriction site and the oligodT stretch.

9. A method of claim 1 wherein in step (b) the double-stranded cDNA library constructed in a vector capable of being converted into single-stranded DNA circles in vivo is converted into the single-stranded DNA circles in vivo.

10. A method of claim 9 wherein the double-stranded cDNA library is converted into the single-stranded DNA circles by transforming the cDNA library into bacteria and infecting the transformed bacteria with helper phage capable of converting the double-stranded cDNA library into the single-stranded DNA circles.

11. A method of claim 10 wherein the bacteria used is *Escherichia coli* DH5αF' and the helper phage used is M13K07.

12. A method of claim 1 wherein in step (b) the double-stranded cDNA library constructed in a vector capable of being converted into single-stranded DNA circles in vitro is converted into the single-stranded DNA circles in vitro.

13. A method of claim 12 wherein the double-stranded cDNA library is converted into the single-stranded DNA circles by digestion with a site-specific endonuclease and an exonuclease.

14. A method of claim 13 wherein the site-specific endonuclease used is the replication initiator protein of bacteriophage f1, Gene II, and the exonuclease used is Exonuclease III.

15. A method to normalize a cDNA library comprising:
   (a) providing a directionally cloned library containing cDNA inserts in circular double-stranded form;
   (b) converting the double-stranded cDNA library into single-stranded DNA circles;
   (c) generating single-stranded nucleic acid molecules complementary to the single-stranded DNA circles converted in step (b) by
      excising cDNA inserts from the double-stranded cDNA library;
      purifying the cDNA inserts from cloning vectors; and
      digesting the cDNA inserts with an exonuclease;

(d) hybridizing the single-stranded DNA circles converted in step (b) with the complementary single-stranded nucleic acid molecules generated in step (c) to produce partial duplexes at an appropriate Cot; and (e) separating unhybridized single-stranded DNA circles from hybridized DNA circles, thereby generating a normalized cDNA library.

16. A method of claim 15 wherein in step (b) the double-stranded cDNA library is converted into the single-stranded DNA circles in vitro.

17. A method of claim 15 wherein in step (b) the double-stranded cDNA library is converted into the single-stranded DNA circles in vivo.

18. A method of claim 15 wherein the exonuclease used is Exonuclease III.

19. A method of claim 1 or 15 wherein the single-stranded DNA circles are separated from the unconverted double-stranded cDNA library.

20. A method of claim 19 wherein the single-stranded DNA circles are separated from the unconverted double-stranded cDNA library by hydroxyapatite column chromatography.

21. A method of claim 15 wherein the single-stranded nucleic acid molecules generated in step (c) comprise the 5' halves of all cDNA inserts of the double-stranded cDNA library used in step (a).

22. A method of claim 1 wherein the single-stranded nucleic acid molecules generated in step (c) span the entire length of the cDNA inserts.

23. A method of claim 1 wherein the single-stranded nucleic acid molecules are generated by PCR amplification of all cDNA inserts of the cDNA library.

24. A method of claim 1 or 15, wherein in step (d) the complementary nucleic acid molecules and the single-stranded DNA circles are hybridized under conditions used for hydroxyapatite column chromatography.

25. A method of claim 24, wherein the complementary nucleic acid molecules and the single-stranded DNA circles are hybridized in a solution comprising 0.12M NaCl-50% formamide-1% SDS-5 mM EDTA pH 8.0 at 30° C. for an appropriate amount of time which corresponds to a Cot of about 5.

26. A method to construct a subtractive cDNA library comprising:

(a) converting a double-stranded circular cDNA library into single-stranded DNA circles;

(b) treating a pool of double-stranded circular DNAs which are to be eliminated from the subtractive cDNA library with a site-specific endonuclease and an exonuclease to generate single-stranded circular DNA molecules;

(c) separating the single-stranded circular DNA molecules from step (a) from double-stranded DNAs;

(d) amplifying inserts of the separated single-stranded DNA molecules derived from step (b) by PCR using appropriate primers to form amplification products;

(e) hybridizing the single-stranded DNA circles derived from step (a) with the amplification products generated in step (d) to produce partial duplexes at an appropriate Cot; and (f) separating unhybridized single-stranded DNA circles from hybridized DNA circles, thereby generating a subtractive cDNA library.

27. A method of claim 26 wherein in step (a) the double-stranded circular cDNA library is converted into the single-stranded DNA circles by treating the double-stranded cDNA circular library with a site-specific endonuclease and an exonuclease.

28. A method of claim 27 wherein the site-specific endonuclease used is the replication initiator protein of bacteriophage f1 (Gene II) and the exonuclease used is Exonuclease III.

29. A method of claim 26 wherein the single-stranded DNA circles are separated from an unconverted double-stranded circular cDNA library by hydroxyapatite column chromatography.

30. A method of claim 26 wherein in step (b) the site-specific endonuclease used is the replication initiator protein of bacteriophage f1 (Gene II) and the exonuclease used is Exonuclease III.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TGTTACCAAT CTGAAGTGGG AGCGGCCGC    29

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AACTGGAAGA ATTCGCGGCC GCAGGAA    27

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AACTGGAAGA ATTAATTAAA GATCT    25

( 2 ) INFORMATION FOR SEQ ID NO:4:

( i ) SEQUENCE CHARACTERISTICS:
        ( A ) LENGTH: 296 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CACCCCAGGC  TTTACACTTT  ATGCTTCCGG  CTCGTATGTT  GTGTGGAATT  GTGAGCGGAT    60

AACAATTTCA  CACAGGAAAC  AGCTATGACA  TGATTACGAA  TTTAATACGA  CTCACTATAG   120

GGAATTTGGC  CCTCGAGGCC  AAGAATTCCC  GACTACGTAG  TCGGGGATCC  GTCTTAATTA   180

AGCGGCCGCA  AGCTTATTCC  CTTTAGTGAG  GGTTAATTTT  AGCTTGGCAC  TGGCCGTCGT   240

TTTACAACGT  CGTGACTGGG  AAAACCCTGG  CGTTACCCAA  CTTAATCGCC  TTGCAG       296
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
AGCGGATAAC  AATTTCACAC  AGGA                                              24
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GACTGGTGAG  TACTCAACCA  AGTC                                              24
```

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
AGGGCGGCCG  CAAGCTTATT  CCCTTTAGTG  AGGGTTAT                              38
```

( 2 ) INFORMATION FOR SEQ ID NO:8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
AGATCTTTAA  TTAAGCGGCC  GCAAGCTTAT  TCCCTTTAGT  GAGGGTTAAT                50
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO:9:

AGGCCAAGAA TTCGGCACGA G                                                                      21

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

CCTCGTGCCG AATTCTTGGC CTCGAGGGCC AAATTCCC                                                    38

(2) INFORMATION FOR SEQ ID NO:11:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:11:

CCTCGTGCCG AATTCTTGGC CTCGAGGGCC AAATTCCCTA TAGTGAGTCG TATTA          55

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:12:

TAATACGACT CACTATAGGG                                                                        20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:13:

ATTAACCCTC ACTAAAGGGA                                                                        20

(2) INFORMATION FOR SEQ ID NO:14:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:14:

-continued

CCTCGTGCCG AATTCTTGGC CTCGAGGGCC AAATTCCCTA TAGTGAGTCG TATTA    55

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

ATTAACCCTC ACTAAAGGGA ATAAGCTTGC GGCCGCT    37

( 2 ) INFORMATION FOR SEQ ID NO:16:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ATTAACCCTC ACTAAAGGGA ATAAGCTTGC GGCCGCTTAA TTAAAGATCT    50